(12) United States Patent
Kilroy et al.

(10) Patent No.: US 10,617,484 B2
(45) Date of Patent: Apr. 14, 2020

(54) HYPERDEXTEROUS SURGICAL SYSTEM USER INTERFACE DEVICES

(71) Applicant: SRI International, Menlo Park, CA (US)

(72) Inventors: Pablo Eduardo Garcia Kilroy, Menlo Park, CA (US); Karen Shakespear Koenig, San Jose, CA (US); Jose Luis Cordoba Matilla, Malaga (ES); Joan Savall, Palo Alto, CA (US)

(73) Assignee: SRI International, Menlo Park, CA (US)

( * ) Notice: Subject to any disclaimer, the term of this patent is extended or adjusted under 35 U.S.C. 154(b) by 30 days.

(21) Appl. No.: 15/790,901

(22) Filed: Oct. 23, 2017

(65) Prior Publication Data

US 2018/0168759 A1    Jun. 21, 2018

Related U.S. Application Data

(63) Continuation of application No. PCT/US2015/052354, filed on Sep. 25, 2015.
(Continued)

(51) Int. Cl.
*G05B 15/00* (2006.01)
*G05B 19/00* (2006.01)
(Continued)

(52) U.S. Cl.
CPC .............. *A61B 34/74* (2016.02); *A61B 34/37* (2016.02); *A61B 34/76* (2016.02); *B25J 3/00* (2013.01);
(Continued)

(58) Field of Classification Search
CPC ...... A61B 2090/065; A61B 2090/0818; A61B 2562/168; A61B 34/37; A61B 34/74;
(Continued)

(56) References Cited

U.S. PATENT DOCUMENTS 5,339,723 A * 8/1994 Huitema ............ A61B 17/1285
                                                  606/206
D375,909 S * 11/1996 Dziersk .................... D10/106.1
(Continued)

FOREIGN PATENT DOCUMENTS

CN        102339148 A     2/2012
CN        102750017 A     10/2012
(Continued)

OTHER PUBLICATIONS

Written Opinion of the International Search Authority dated Jan. 7, 2016 for WO Application No. PCT/US15/052354.
(Continued)

*Primary Examiner* — Harry Y Oh
(74) *Attorney, Agent, or Firm* — Womble Bond Dickinson (US) LLP

(57) ABSTRACT

User interface devices are disclosed. The device can include a body that can be held in a user's hand. The body has an outer surface that can be gripped by fingers of the user's hand to facilitate translation and rotation of the body by the user's hand. The device can include one or snore sensors disposed within the body. In some embodiments, the one or more sensor can provide one or both of position and orientation information of the body to a control system. The body can provide feedback to the user via the exterior surface of the body that is gripped by the user's fingers and/or can receive control inputs from the user via one or more of translation of the body, rotation of the body, pressing of the outer surface with the user's fingers, and changing of the angular orientation of the longitudinal axis of the body. Methods of using a user interface device are also provided.

21 Claims, 9 Drawing Sheets

Related U.S. Application Data

(60) Provisional application No. 62/151,596, filed on Apr. 23, 2015.

(51) Int. Cl.
| | |
|---|---|
| *A61B 34/00* | (2016.01) |
| *A61B 34/37* | (2016.01) |
| *B25J 3/00* | (2006.01) |
| *B25J 13/02* | (2006.01) |
| *B25J 13/08* | (2006.01) |
| *A61B 90/00* | (2016.01) |
| *A61B 17/00* | (2006.01) |

(52) U.S. Cl.
CPC ........... *B25J 13/025* (2013.01); *B25J 13/086* (2013.01); *A61B 2017/00207* (2013.01); *A61B 2017/00212* (2013.01); *A61B 2090/064* (2016.02); *A61B 2090/065* (2016.02); *A61B 2090/067* (2016.02); *A61B 2090/0818* (2016.02); *A61B 2562/168* (2013.01); *Y10S 901/02* (2013.01); *Y10S 901/46* (2013.01)

(58) Field of Classification Search
CPC ....... A61B 34/76; B25J 13/025; B25J 13/086; B25J 3/00; Y10S 901/02; Y10S 901/46
See application file for complete search history.

(56) References Cited

U.S. PATENT DOCUMENTS

| | | | | |
|---|---|---|---|---|
| 5,720,742 | A * | 2/1998 | Zacharias | A61B 17/29 606/1 |
| 6,270,508 | B1 * | 8/2001 | Klieman | A61B 17/062 606/147 |
| 9,439,733 | B2 * | 9/2016 | Ha | A61B 34/37 |
| 2008/0154246 | A1 * | 6/2008 | Nowlin | B25J 9/1689 606/1 |
| 2008/0174550 | A1 * | 7/2008 | Laurila | A63F 13/02 345/158 |
| 2009/0022432 | A1 * | 1/2009 | Unda | H04B 1/202 383/67 |
| 2009/0267897 | A1 * | 10/2009 | Ootsuka | G08C 17/02 345/158 |
| 2011/0118752 | A1 * | 5/2011 | Itkowitz | B25J 9/1689 606/130 |
| 2012/0256739 | A1 * | 10/2012 | Kawabe | B25J 13/025 340/407.2 |
| 2013/0063580 | A1 * | 3/2013 | Ogawa | B25J 9/1689 348/65 |
| 2014/0005682 | A1 * | 1/2014 | Worrell | A61B 18/1442 606/130 |
| 2016/0121093 | A1 * | 5/2016 | Fan | H04W 4/80 606/185 |
| 2016/0279802 | A1 * | 9/2016 | Kietzman | B25J 13/006 |

FOREIGN PATENT DOCUMENTS

| | | |
|---|---|---|
| DE | 102007022120 A1 | 11/2008 |
| EP | 2407862 A1 | 1/2012 |
| EP | 2743801 A2 | 6/2014 |
| EP | 3285673 A1 | 2/2018 |
| JP | 2005267174 A | 9/2005 |
| WO | WO2014/151621 A1 | 9/2014 |
| WO | 2016/171757 A1 | 10/2016 |

OTHER PUBLICATIONS

Outgoing—ISA/210—International Search Report dated Jan. 7, 2016 for WO Application No. PCT/US15/052354.
(IPEA/409) International Preliminary Report on Patentability Chapter II or (IB/373) International Preliminary Report on Patentability Chapter I dated Nov. 2, 2017 for WO Application No. PCT/US15/052354.
European Search Report and Written Opinion dated May 23, 2019 for related European Appln. No. EP 15 89 0149 17 Pages.
Nat Kerris et al; Apple Announces iPhone 6 & iPhone 6 Plus—Press Release; Cupertino, CA; 4 Pages (Sep. 9, 2014) <https://www.apple.com/newsroom/2014/09/09Apple-Announces-iPhone-6-iPhone-6-Plus-The-Biggest-Advancements-in-iPhone-History/>.
First Office Action for counterpart Chinese Patent Application No. 201580080006.7 with English translation, 18 pgs. (dated Oct. 9, 2019).
First Examination Report for counter Australian Patent Application No. 2015392228, 3 pgs. (dated Oct. 18, 2019).

* cited by examiner

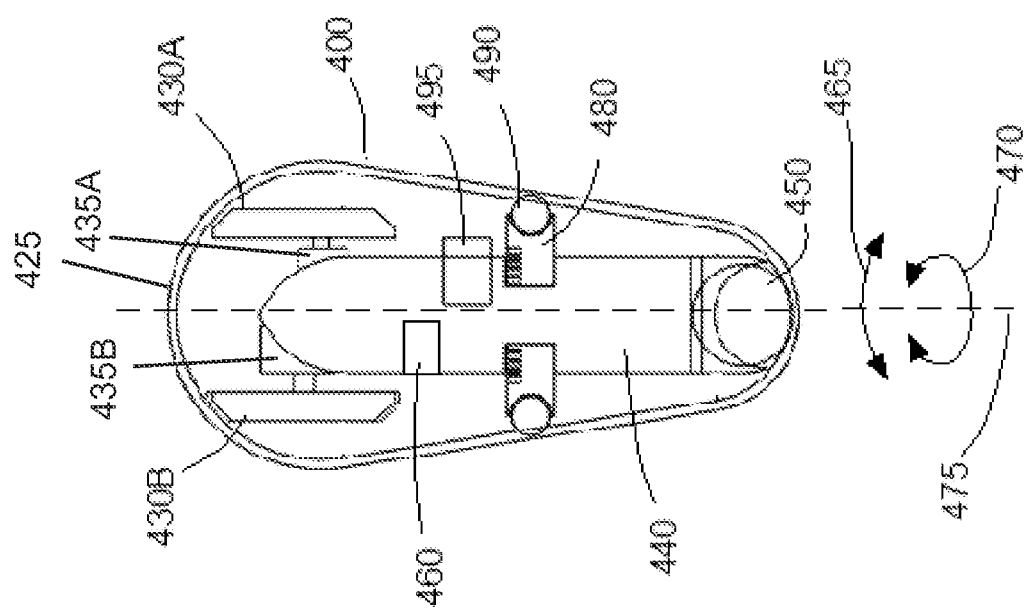

HYPERDEXTEROUS SURGICAL SYSTEM USER INTERFACE DEVICES

CROSS-REFERENCE TO RELATED APPLICATIONS

This application is a continuation of International Application No. PCT/US2015/052354, filed Sep. 25, 2015 and hereby incorporated by reference herein in its entirety and should be considered a part of this specification, which claims the priority benefit under 35 U.S.C. § 119(e) of U.S. Provisional Application No. 62/151,596 filed Apr. 23, 2015, which is hereby incorporated by reference herein in its entirety and should be considered a part of this specification. This application hereby incorporates by reference herein in its entirety International Application No. PCT/US2014/026115, filed Mar. 13, 2014 designating the U.S. and published in English on Sep. 25, 2014 as WO 2014/151621, which should be considered a part of this specification. This application hereby incorporates by reference herein in its entirety U.S. Provisional Application No. 62/120,128, filed Feb. 24, 2015, which should be considered a part of this specification.

BACKGROUND

Field

Surgical robots allow surgeons to operate on patients in a minimally invasive manner. The present application relates to surgical systems and methods, and more particularly to user interface devices for hyperdexterous surgical systems with one or more hyperdexterous surgical arms and one or more end effectors, and methods of operating the same.

Description of the Related Art

The use of robots is growing and proliferating in all aspects of life. Some robots are autonomous in that human intervention is not needed beyond just starting the robot and instructing the robot to do a set of tasks. Some other robots are controlled by a human operator. The on-market robotic systems used for surgery are an example of the later kind, where an operator controls the robot.

Typically such systems have a console from which an operator can manipulate the robot. Therefore, the surgeon is located remotely from the patient when using on-market robotic surgical systems, often sitting at a remote console. Typically on-market systems use mechanically grounded user interface devices. Typically these grounded user interface devices are fixed in space to a user console. The grounded user interface devices convey a sense of orientation and direction. The grounded user interface devices are not manipulated in free space.

In on-market systems, the grounded user interface devices can provide feedback in various situations such as when the robotic system reaches a joint limit. Feedback may be provided by the user simply feeling that the user input devices are hard to move. In more advanced methods the robotic system may deliberately impose a motion on the grounded user interface device to provide the feedback.

The main function of the grounded user interface device is to provide the operator with the capability of manipulating tools and end effectors with dexterity. In on-market robotic surgical systems, a large robotic arm controls a robotic tool. The tool is inserted into a small incision. The distal end of the robotic tool typically includes an end effector (e.g., a grasper, stapler, etc.) for performing a procedure within the body of the patient. The end effector is translated in space, within the constraints of the capabilities of the robotic arm. The surgeon typically controls the robotic arm from an immersive console that is remote from the patient. The robotic tool can do certain surgical tasks well, but is not well-suited for other surgical tasks.

In on-market surgical robotic systems, the motions of the robotic tool are generally viewed via a robotic camera. The motions of the robotic camera are controlled by a robotic arm, also under control of the surgeon like other robotic tools. The movements of the surgeon's hand controlling the grounded user interface device can be mapped to the movement of the robotic tool in the frame of reference of the camera. The motions of the grounded user interface device are mapped to the distal end effectors of the robotic tools within the frame of reference of the robotic camera. The reference information provided to the surgeon is therefore limited to the view provided by the camera. The display typically shows the motion of the distal end of the robotic tools strictly from the point of view of the camera held by the robot.

The surgeon must therefore create a mental model of the anatomy with the limited information provided by the camera to control the robotic tools as desired for a particular task. Due to his remote location at the console, the surgeon cannot acquire additional views of the patient in order to augment his understanding of the surgical space. The limited point of view from the robotic camera makes aspects of the surgery less natural. For example, making large movements from one quadrant of the abdomen to another, especially motions that involve the camera sweeping through an arc that includes the midline of the patient, are very challenging.

Typically, the surgeon views the surgery site and tools through a viewer which provides an immersive experience. In some cases, communication between the surgeon and the supporting staff is constrained or impeded due to the surgeon's position over the console. Teams that perform robotic surgery need to be highly trained and skilled since the surgeon is remote from the patient and unable to communicate with the staff directly. It takes months, in some cases years, of practice to achieve a high level of efficiency in situations where robotic surgery is performed. This makes it difficult for members of the team to be replaced. Additionally, from this remote location (at the console), the surgeon cannot simultaneously use manual tools while controlling the robot arm.

A drawback of the current systems is that they provide limited information to the surgeon. Typically this information is limited to the view of a robotic camera. The surgeon cannot view the patient while using the grounded user interface devices. The surgeon cannot receive feedback about the patient's anatomy. The surgeon cannot use manual tools or touch the patient while using the grounded user interface devices. Another drawback with on-market robotic surgical systems is that they do not allow the surgeon the ability to reposition him or herself during surgery. The surgeon must remain at the immersive console to manipulate the grounded user interface device to perform a surgical task with the end effectors of the robotic tools.

SUMMARY

There is a need for user interface devices that overcome the deficiencies discussed above with on-market robotic surgical systems and provide flexibility to surgeons when performing surgical procedures.

The user interface devices provide advantages over on-market user interface devices described above. One aspect of the groundless and body grounded user interface devices is that these devices are manipulated in free space. The groundless and body grounded user interface devices are advantageously not constrained to a console. The groundless and body grounded user interface devices can be manipulated at a natural height for the user while standing or sitting, and can advantageously be manipulated while the surgeon moves about the operating theater.

One aspect of the groundless and body grounded user interface devices is that these devices can be wired or wireless. Wireless groundless and body grounded user interface devices may advantageously allow the user to freely move about the operating arena without the constraint of wires. Wired groundless and body grounded user interface devices may provide a more reliable connection to convey signals and information from the groundless and body grounded user interface devices.

One aspect of the groundless and body grounded user interface devices is that these devices can have shape that provides a sense of orientation. The groundless and body grounded user interface devices can include an interface or surface upon which the user can place his or her fingers. The groundless and body grounded user interface devices can have an elongate shape. For instance, the ends of the elongate shape can provide a sense of orientation (e.g., front, back). For instance, the surface of the groundless and body grounded user interface devices can provide a sense of orientation (e.g., top, bottom).

One aspect of the groundless and body grounded user interface devices is that these devices provide versatility on where the groundless and body grounded user interface devices can be operated. The groundless and body grounded user interface devices are advantageously portable and movable with the surgeon. The groundless and body grounded user interface devices can be used from any position and/or orientation relative to the patient within the operating arena. The groundless and body grounded user interface devices can be operated adjacent to the patient. The groundless and body grounded user interface devices can be operated at a location apart from the patient, such as at a console. The groundless and body grounded user interface devices can be operated as the user reorients himself or herself relative to the patient.

One aspect of the groundless and body grounded user interface devices is that these devices can provide feedback to the user. The groundless and body grounded user interface devices can provide feedback on movement limits of, for example, a hyperdexterous surgical system. The groundless and body grounded user interface devices can provide feedback of a joint limit. The groundless and body grounded user interface devices can provide feedback about the surgical space. The groundless and body grounded user interface devices can provide feedback when the end effector collides with or has the potential to collide with a hard object. The groundless and body grounded user interface devices can provide feedback on the hardness or softness of objects that the end effector is touching. The groundless and body grounded user interface devices can provide feedback in the form of pressure. The groundless and body grounded user interface devices can provide feedback in the form of sound. The groundless and body grounded user interface devices can provide visual feedback, such as in the form of light.

One aspect of the groundless and body grounded user interface devices is that these devices can inhibit injury to the patient. The groundless and body grounded user interface devices can advantageously to prevent the end effector from following the groundless and body grounded user interface devices, such as when the groundless and body grounded user interface devices are inadvertently dropped. The groundless and body grounded user interface devices can provide impedance information. The impedance value will change when the user drops the groundless and body grounded user interface devices. The hyperdexterous surgical system can prevent the end effector from following the motion of the groundless and body grounded user interface devices when the impedance value crosses a threshold. The groundless and body grounded user interface devices can provide acceleration information. The acceleration will change when the user drops the groundless and body grounded user interface devices. The hyperdexterous surgical system can prevent the end effector from following the motion of the groundless and body grounded user interface devices when the acceleration value crosses a threshold.

In some embodiments, a handheld portable user interface device is disclosed. The device can include a body configured to be held in a user's hand. In some embodiments, the body comprises a proximal portion and a distal portion and extending along a length defined by a longitudinal axis between a proximal end and a distal end of the body. In some embodiments, the body extends along a width defined along a transverse axis that extends transverse to the longitudinal axis. In some embodiments, the length is greater than the width of the body. In some embodiments, the body comprises an outer surface configured to be gripped by fingers of the user's hand and to facilitate translation and rotation of the body by the user's hand. The device can include one or more sensors disposed within the body. In some embodiments, the one or more sensor is configured to provide one or both of position and orientation information of the body to a control system. In some embodiments, the body is configured to receive control inputs from the user via one or more of translation of the body, rotation of the body, pressing of the outer surface with the user's fingers, and changing of the angular orientation of the longitudinal axis of the body.

In some embodiments, the body is configured to provide tactile feedback to the user via the outer surface of the body that is gripped by the fingers of the user's hand. In some embodiments, the user interface device is supported solely by the user's hand. In some embodiments, the user interface device is configured to provide an input to the control system to transform motion of the user interface device into motion of an end effector of a robotic arm. In some embodiments, the one or more sensors provide redundancy of function. In some embodiments, the one or more sensors are of different types. In some embodiments, the one or more sensors include a proximity sensor. In some embodiments, the outer surface is configured to be depressed by the user. In some embodiments, the body comprises a chamber configured to be filled with a fluid, wherein depression of the outer surface by the user causes sensed pressure in the chamber to change, said change in sensed pressure communicated to the control system to convert the sensed pressure into a force applied by an end effector of a robotic arm controlled with the body. In some embodiments, the body further comprises a pump configured to change the pressure of the chamber to provide tactile feedback to the user.

In some embodiments, a handheld user interface device is disclosed. The device can include a body configured to be held in a user's hand and supported solely by the user's hand. Optionally, the body can also be supported by the user's arm. In some embodiments, the body comprises an exterior surface configured to be gripped by fingers of the user's hand to facilitate translation and rotation of the body by the user's hand. The device can include one or more sensors disposed within the body. In some embodiments, the one or more sensor configured to provide one or both of position and orientation information of the body to a control system. In some embodiments, the body is configured to provide feedback to the user via the exterior surface of the body that is gripped by the user's fingers.

In some embodiments, the body is configured to receive control inputs from the user via one or more of translation of the body, rotation of the body, pressing of the exterior surface with the user's fingers, and changing of the angular orientation of the longitudinal axis of the body. The device can optionally include an internal chassis configured to move within an outer skin of the body to adjust an orientation of the longitudinal axis of the user interface device. In some embodiments, the internal chassis moves relative to the outer skin to attain a desired pitch and/or yaw orientation and communicates this to the user haptically. In some embodiments, the internal chassis moves in one of the following ways selected from the group consisting of expansion, retraction, pulsing, and rotation. In some embodiments, the internal chassis has one or more actuators that effect the motion of the internal chassis. In some embodiments, the one or more actuators comprise a ring actuatable to attain a desired roll orientation. In some embodiments, the internal chassis adjusts pitch, yaw and/or roll orientation to maintain alignment of the longitudinal axis of the user interface device axis with an axis of a device, such as an end effector, controlled by the user interface device. In some embodiments, the internal chassis adjusts pitch, yaw and/or roll orientation in response to forces on the device (e.g., end effector) controlled by the user interface device. In some embodiments, the body comprises one or more actuators for changing of the shape of the body. In some embodiments, the body comprises one or more pressure chambers for changing of the shape of the body.

In some embodiments, a method of using a handheld portable user interface device is disclosed. The method can include the step of holding a body of the user interface device with the user's hand. In some embodiments, the body comprises a proximal portion and a distal portion and extends along a length defined along the longitudinal axis between a proximal end and a distal end of the body. In some embodiments, the body extends along a width defined along a transverse axis that extends transverse to the longitudinal axis. In some embodiments, the length is greater than the width of the body. In some embodiment, the device includes one or more sensors disposed within the body that provides orientation information of the body to a control system. The method can include the step of generating control signals from one or more of translating of the body, rotating of the body, pressing of the outer surface with the user's fingers, and changing of the angular orientation of the longitudinal axis of the body.

The method can include the step of communicating said control signals to a control system to control the operation of a device, such as an end effector of a robotic arm, with the user interface device. The method can include the step of transforming the motion of the user interface device into motion of the device (e.g., end effector) controlled with the user interface device. The method can include the step of receiving control signals to move a chassis within the body of the user interface device. The method can include the step of moving the chassis within the body to adjust an orientation of the longitudinal axis of the user interface device. The method can include the step of moving the chassis to attain a desired pitch and/or yaw orientation of an axis of an end effector controlled by the user interface device. The method can include the step of moving the internal chassis in one of the following ways selected from the group consisting of expansion, retraction, pulsing, and rotation. The method can include the step of actuating a ring to attain a desired roll orientation of an axis of an end effector controlled by the user interface device. The method can include the step of adjusting a pitch, yaw and/or roll orientation of the chassis to maintain alignment of the longitudinal axis of the user interface device axis with an axis of a device (e.g., an end effector) controlled by the user interface device. The method can include the step of adjusting a pitch, yaw and/or roll orientation of the chassis in response to forces on said device (e.g., the end effector). The method can include the step of operating the user interface device in a drive mode wherein the end effector is moved by the user interface device. The method can include the step of operating the user interface device in a non-drive mode wherein the chassis of the user interface device maintains alignment of the longitudinal axis of the user interface device axis with an axis of the end effector despite movements of the user interface device by the user. In some embodiments, movement of the chassis provides feedback on a joint limit. In some embodiments, movement of the chassis provides feedback on the force experienced by an end-effector. In some embodiments, holding the body comprises supporting the body solely with the user's hand. In some embodiments, pressing of the outer surface with the user's fingers generates a pressure signal that a control system converts into a force applied by an end effector of a robotic arm. In some embodiments, pressing of the outer surface with the user's fingers further comprises pressing of the outer surface at any rotational position of the body.

According to an aspect of the present in invention, there is provided a handheld portable user interface device, comprising a body configured to be held in a user's hand, the body comprising a proximal portion and a distal portion and extending along a length defined by a longitudinal axis between a proximal end and a distal end of the body, the body extending along a width defined along a transverse axis that extends transverse to the longitudinal axis, the length being greater than the width of the body, the body comprising an outer surface configured to be gripped by fingers of the user's hand and to facilitate translation and rotation of the body by the user's hand; and one or more sensors disposed within the body, the one or more sensors configured to provide one or both of position and orientation information of the body to a control system, wherein the body is configured to receive control inputs from the user via one or more of translation of the body, rotation of the body, pressing of the outer surface with the user's fingers, and changing of the angular orientation of the longitudinal axis of the body.

The device may be arranged such that the body is configured to provide tactile feedback to the user via the outer surface of the body that is gripped by the fingers of the user's hand.

The device may be arranged such that the user interface device is supported solely by the user's hand.

The device may be arranged such that the user interface device is configured to provide an input to the control system to transform motion of the user interface device into motion of an end effector of a robotic arm.

The device may be arranged such that the one or more sensors provides redundancy of function.

The device may be arranged such that the one or more sensors are of different types.

The device may be arranged such that the one or more sensors includes a proximity sensor.

The device may be arranged such that the outer surface is configured to be depressed by the user.

The device may be arranged such that the body comprises a chamber configured to be filled with a fluid, wherein depression of the outer surface by the user causes sensed pressure in the chamber to change, said change in sensed pressure communicated to the control system to convert the sensed pressure into a force applied by an end effector of a robotic arm controlled with the body.

The device may be arranged such that the body further comprises a pump configured to change the pressure of the chamber to provide tactile feedback to the user.

According to another aspect of the present invention, there is provided a handheld user interface device, comprising: a body configured to be held in a user's hand and supported solely by the user's hand, the body comprising an exterior surface configured to be gripped by fingers of the user's hand to facilitate translation and rotation of the body by the user's hand; and one or more sensors disposed within the body, the one or more sensors configured to provide one or both of position and orientation information of the body to a control system, wherein the body is configured to provide feedback to the user via the exterior surface of the body that is gripped by the user's fingers.

The device may be arranged such that the body is configured to receive control inputs from the user via one or more of translation of the body, rotation of the body, pressing of the exterior surface with the user's fingers, and changing of the angular orientation of the longitudinal axis of the body.

The device may be arranged such that the device further comprises an internal chassis configured to move within an outer skin of the body to adjust an orientation of the longitudinal axis of the user interface device.

The device may be arranged such that the internal chassis moves relative to the outer skin to attain a desired pitch and/or yaw orientation and communicates this to the user haptically.

The device may be arranged such that the internal chassis moves in one of the following ways selected from the group consisting of expansion, retraction, pulsing, and rotation.

The device may be arranged such that the internal chassis has one or more actuators that effect the motion of the internal chassis.

The device may be arranged such that the one or more actuator comprises a ring actuatable to attain a desired roll orientation.

The device may be arranged such that the internal chassis adjusts pitch, yaw and/or roll orientation to maintain alignment of the longitudinal axis of the user interface device axis with an axis of an end effector controlled by the user interface device.

The device may be arranged such that the internal chassis adjusts pitch, yaw and/or roll orientation in response to forces on the end effector.

The device may be arranged such that the body comprises one or more actuators for changing of the shape of the body.

The device may be arranged such that the body comprises one or more pressure chambers for changing of the shape of the body.

According to another aspect of the present invention, there is provided a method of using a handheld portable user interface device, comprising: holding a body of the user interface device with the user's hand, the body comprising a proximal portion and a distal portion and extending along a length defined along the longitudinal axis between a proximal end and a distal end of the body, the body extending along a width defined along a transverse axis that extends transverse to the longitudinal axis, the length being greater than the width of the body, wherein one or more sensors disposed within the body provides orientation information of the body to a control system, and generating control signals from one or more of translating of the body, rotating of the body, pressing of the outer surface with the user's fingers, and changing of the angular orientation of the longitudinal axis of the body.

The method may include communicating said control signals to a control system to control the operation of an end effector of a robotic arm with the user interface device.

The method may include transforming the motion of the user interface device into motion of the end effector.

The method may include receiving control signals to move a chassis within the body of the user interface device.

The method may include moving the chassis within the body to adjust an orientation of the longitudinal axis of the user interface device.

The method may include moving the chassis to attain a desired pitch and/or yaw orientation of an axis of an end effector controlled by the user interface device.

The method may include moving the internal chassis in one of the following ways selected from the group consisting of expansion, retraction, pulsing, and rotation.

The method may include actuating a ring to attain a desired roll orientation of an axis of an end effector controlled by the user interface device.

The method may be include adjusting a pitch, yaw and/or roll orientation of the chassis to maintain alignment of the longitudinal axis of the user interface device axis with an axis of an end effector controlled by the user interface device.

The method may include adjusting a pitch, yaw and/or roll orientation of the chassis in response to forces on the end effector.

The method may include operating the user interface device in a drive mode wherein the end effector is moved by the user interface device.

The method may include operating the user interface device in a non-drive mode wherein the chassis of the user interface device maintains alignment of the longitudinal axis of the user interface device axis with an axis of the end effector despite movements of the user interface device by the user.

The method may be arranged such that movement of the chassis provides feedback on a joint limit.

The method may be arranged such that movement of the chassis provides feedback on the force experienced by an end-effector.

The method may be arranged such that holding the body comprises supporting the body solely with the user's hand.

The method may be arranged such that pressing of the outer surface with the user's fingers generates a pressure signal that a control system converts into a force applied by an end effector of a robotic arm.

The method may be arranged such that pressing of the outer surface with the user's fingers further comprises pressing of the outer surface at any rotational position of the body.

Unless otherwise stated, or unless clearly incompatible, each embodiment of this invention may comprise, additional to its essential features described herein, one or more features as described herein from each other embodiment of the invention.

BRIEF DESCRIPTION OF THE DRAWINGS

FIG. 6A is a cross-sectional view of an embodiment of a groundless user interface device.

DETAILED DESCRIPTION

Figure 1A:
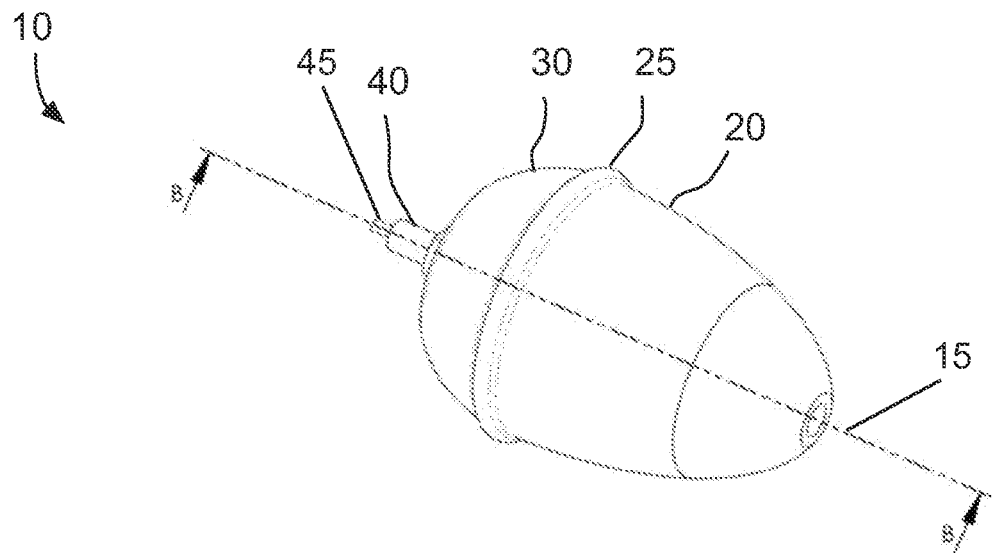
FIG. 1A schematically illustrates an embodiment of a groundless user interface device.

International Application No. PCT/US2014/026115 filed Mar. 13, 2014 designating the US and published in English on Sep. 25, 2014 as WO 2014/151621 describes various hyperdexterous surgical systems. This application is incorporated by reference herein. This application describes a new type of robotic system. The hyperdexterous surgical system overcomes deficiencies of typical on-market robotic systems. However, the versatility of the user interface device needs to match the versatility of the movement of the tools or end effectors of the hyperdexterous surgical systems. Thus disclosed herein are user interface devices that are able to control the hyperdexterous surgical systems with versatility. The user interface device can control end effectors or tools. Examples of end effectors include graspers or jaws. An end effector, as used herein, should be understood to include any of the following: (1) the most distal portion of a robotic arm, typically the portion which is interacting with the operative environment; (2) a simulated or virtual version of (1); and/or (3) a 2D or 3D mouse, stylus, pointer, etc. designed to facilitate user interaction with a virtual environment or any other 3D or 2D dataset, such as MRI or CT scan data. The user interface devices described herein is a multi-purpose 3D input device. In some embodiments, the user interface devices described herein can control a physical robot.

Disclosed herein are at least two new types of user interface devices. One new category of user interface devices is body grounded user interface devices. Body grounded user interface devices are advantageously coupled to a portion of the user's body. This portion can be movable with the body of the user, such as the hand of the surgeon. Another new category of user interface devices is groundless user interface devices. Groundless user interface devices may be wired or wireless. These two new categories may be contrasted with user interface devices found in typical on-market systems, which may be categorized as grounded user interface devices. These new two categories provide a way to control the hyperdexterous robotic system in a versatile manner.

Body grounded user interface devices or groundless user interface devices introduce a very different paradigm for controlling a robotic system, especially one that is used for surgery. One difference between a grounded user interface devices and a body grounded user interface devices or a groundless user interface devices is that the latter two are advantageously manipulated in free space unlike the grounded user interface devices. While conveying a sense of orientation and direction, the body grounded user interface devices and the groundless user interface devices provide the operator the capability to manipulate tools and end effectors with dexterity—the main function of the user interface devices. There is a need to provide feedback for various situations exists for the body grounded user interface devices and for the groundless user interface devices.

There are other needs that are brought about due to the ungrounded nature of both the body grounded user interface devices and the groundless user interface devices. One need is related to safety especially as it relates to the groundless user interface devices. For instance, if a groundless user interface device was to accidently fall, protections need to be in place to prevent the hyperdexterous robotic arm from following the falling user interface device and thus injuring the patient. These are some of the needs for the user interface devices in order to take advantage of the versatility offered by such systems.

As noted above, two main types of user interface devices are described herein: groundless user interface devices and body grounded user interface devices. The shape of the user interface devices can be selected to provide a sense of orientation and to provide versatile manipulation. Low cost materials can be used so that the user interface devices may be disposable. Disposable user interface devices also address the sterility issue. If the user interface devices are low cost and disposable, sterility may be ensured when the operator opens the package and uses the user interface devices, just as any other disposable tool. Thus the low cost design addresses the sterility need. Mechanisms are also described that provide tactile feedback to user. Both types of user interface devices may have sensors that provide real time information to the user and the hyperdexterous robotic system. For example, in case one of the user interface devices were to fall, the sensors may provide information to the hyperdexterous robotic system such that the corresponding tool does not follow the movements of the user interface device thus preventing injury to the patient.

The benefits of groundless user interface devices and the body grounded user interface devices are numerous. These user interface devices advantageously allow the operator to be close to the patient. The operator can assume a convenient location in relation to the patient's anatomy during a surgical procedure. Further, the operator can assume a different location in relation to the patient's anatomy as the surgical procedure progresses. Due to freedom of movement provided by such user interface devices, an operator, such as a surgeon, can operate one or more user interface devices to perform a combination of manual and robotic surgery, or perform just robotic surgery.

FIG. 1A shows an embodiment of a groundless user interface device (UID) 10. The groundless user interface device 10 can have a body with multiple sections. The embodiment shown in FIG. 1A has three sections, a first section 20, a second section 30, and a third section 40. The body can have any number of sections. The sections can have different configurations. The sections can have the same configuration. The first section 20 can be tapered. The first section 20 can provide a surface for the fingers of the user to grasp the user interface device 10. The first section 20 can be contoured. The first section 20 can include grooves for the fingers. The first section 20 can be a bottom section of the groundless user interface device 10. Other configurations of the first section 20 are contemplated. The second section 30 can be tapered. The second section 30 can be a top section of the groundless user interface device 10. The third section 40 can house a magnetic position sensor, as described herein. The groundless user interface device 10 can be wired (not shown) or wireless. The wires may be used for supplying power to the user interface device 10. The wires may be used for carrying signals (e.g., signals associated with a magnetic position sensor of the UID 10). For instance, the wires may be used for carrying the signals to the control system, described herein. In some embodiments, the user interface device 10 may be wireless.

In some embodiments, the body can be an ovoid body. The body can be egg-shaped. The body can have an oval form. In some embodiments, the body has at least one axis of symmetry. In some embodiments, the shape of the body slightly departs from the shape of the ellipse, with one end having a different curvature than the other end. The first section 20 can approximate the shape of a prolate spheroid. The second section 30 can approximate the shape of a spherical ellipsoid. The second section 30 can approximate a slightly oblate spheroid. The first section 20 and the second section 30 can have two different radii.

The body of the groundless user interface device 10 can be portable. In other embodiments, the user interface devices described herein are not portable. The user interface device can be coupled to a support. The user interface device can be coupled to a cord extending from a support. The user interface device can be coupled to a robotic console.

Figure 1B:
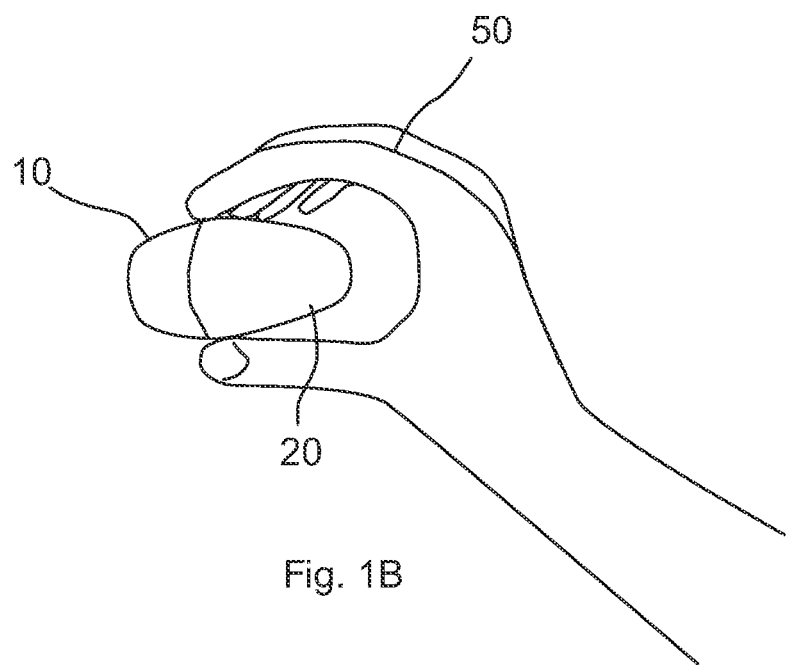
FIG. 1B schematically illustrates a user interacting with the groundless user interface device of FIG. 1A.

FIG. 1B illustrates how such a groundless user interface device 10 may be held advantageously by a human hand 50. The user interface device 10 may be wired or wireless. For convenience, FIG. 1B does not show the wires. The shape of the user interface device 10 is such that the user interface device 10 may be effectively moved only with the user's fingers in addition to being able to move the user interface device 10 with the user's wrist. The ability of being able to move the user interface device 10 only with the fingers provides enhanced dexterity.

The elongated shape of the groundless user interface device 10 may also provide a sense of direction and orientation. The groundless user interface device 10 has a central axis 15 shown in FIG. 1A. The central axis 15 extends from the first section 20 to the third section 40. The central axis extends along the longitudinal axis of the elongate groundless user interface device. In some embodiments, the central axis 15 is an axis of symmetry. In some embodiments, the longitudinal axis of a robotic tool can be controlled by controlling the user interface device 10 along the central axis 15 of the user interface device 10. Also in many cases, the central axis 15 of the user interface device 10 may be used to control the rolling motion of the tool.

The groundless user interface device 10 can be bullet shaped. In some embodiments, the first section 20 can be hemispherical or generally hemispherical. In some embodiments, the first section 20 is conical or generally conical. In some embodiments, the first section 20 is parabolic or generally parabolic. The first section 20 can be divided into one or more subsection. The subsections can have different shapes and/or serve different functions. FIG. 1A shows a subsection of the first section 20 near the end of the groundless user interface device 10 and a subsection of the first section 20 near the lip 25. The subsection near the lip can be positioned over a chamber as described herein. The subsections can have different radii of curvature. In some embodiments, the second section 30 is hemispherical or generally hemispherical. In some embodiments, the third section 40 is cylindrical or generally cylindrical.

The groundless user interface device 10 includes a proximal end that can be held near the palm of the user's hand. The groundless user interface device 10 includes a distal end pointed away from the palm of the user. The central axis 15 of the user interface device 10 extends from the proximal end to the distal end. The central axis 15 can also be called an elongate axis or an axis of symmetry. The central axis 15 is along the length of the groundless user interface device 10. The groundless user interface device 10 has a transverse axis extending transverse (e.g., at 90 degrees) to the elongate axis 15. The transverse axis is along the width of the groundless user interface device 10. The groundless user interface device 10 has an elongate dimension along the elongate axis and a transverse dimension along the transverse axis. In some embodiments, the elongate dimension is greater than the transverse dimension. This creates an oblong shape of the groundless user interface device 10. In some embodiments, the elongate dimension is about twice the transverse dimension. Other dimensions are contemplated (e.g., the elongate dimension is about 1.5 times the transverse dimension, the elongate dimension is about 3 times the transverse dimension, the elongate dimension is about 4 times the transverse dimension, etc.).

The central axis 15 optionally extends generally parallel to an axis of a finger of the user when the user is holding the groundless user interface device 10. The central axis 15 generally aligns with the axis of the user's hand when the user is holding the groundless user interface device 10. The central axis 15 can optionally generally align with the axis of the forearm when the user is holding the groundless user interface device 10.

The groundless user interface device 10 includes a generally circular cross-section along the transverse plane creating a rounded exterior surface. This can be the exterior surface of the first section 20, the second section 30, or the first section 20 and the second section 30. The first section 20 can have a different radius of curvature than the second section 30. This different shape can allow the user to position the first section 20 near the palm of the hand and the second section 30 away from the palm. The exterior surface allows a user to rotate (e.g., about the central axis 15) the groundless user interface device 10 with a hand of the user. The exterior surface allows the user to rotate the groundless user interface device 10 360 degrees. The user can turn the groundless user interface device 10 clockwise or counterclockwise.

The exterior surface of the groundless user interface device 10 has at least one surface to enhance grip of the interface device 10 by the user. The at least one surface can be the lip 25. The lip 25 can extend around the entire groundless user interface device 10 or a portion of the groundless user interface device 10.

In use, the exterior surface of the groundless user interface device 10 can be depressed by the user, as described herein. For example, at least a portion of the exterior surface of the groundless user interface device 10 can be squeezed by the user's fingers. The groundless user interface device 10 can optionally include a chamber, described herein. The chamber can be filled with fluid (e.g., a liquid). The user can depress the chamber from the exterior surface (e.g., by pushing on the surface of the interface device 10 with his or her fingers). The groundless user interface device 10 can optionally include a pump. The pump can change the pressure of the chamber to provide tactile feedback to the user, as described herein. The sensed pressure in the chamber from the user pressing on the exterior surface of the user interface device 10 is converted by the control system to a force applied by the end effector.

The size of the groundless user interface device 10 allows the user to translate the groundless user interface device 10 with the hand of the user. In some embodiments, the user interface device is supported solely by the hand of the user.

The groundless user interface device 10 can optionally include one or more sensors. The sensors can provide orientation information about the groundless user interface device 10 to a control system. The groundless user interface device 10 can provide an input to a control system to transform motion of the user interface device into motion of an end effector of a robotic arm.

The method of using the device can be illustrated in FIG. 1B. The user can hold the body of the user interface device 10 as shown. The user can rotate the exterior surface of the body with a hand. The user can rotate and translate the body with the hand. The sensor disposed within the body can provide orientation information about the user interface device to a control system during one or more of the holding, rotating, or translating steps. The method can include the step of transforming the motion of the user interface device into motion of an end effector of a robotic arm. The method can include the step of gripping the lip 25 of the body. The method can include the step of depressing the exterior surface of the body. The method can include the step of converting the pressure exerted on the exterior surface of the body by the user's hand into a force applied by an end effector of a robotic arm. The method can include the step of depressing the exterior surface by the user at any rotational position (e.g., about the central axis 15) of the user interface device. The method can include the step of filling a chamber of the body with a fluid (e.g., a liquid). The method can include the step of depressing the chamber from the exterior surface (e.g., the user depressing the chamber by pressing on the exterior surface of the body). The method can include the step of converting the pressure of the chamber into a force applied by an end effector of a robotic arm. The method can include the step of changing the pressure of the chamber with a pump to provide tactile feedback to the user (e.g., via a change in pressure exhibited in the chamber and communicated to the user's hand gripping the body).

Figure 2:
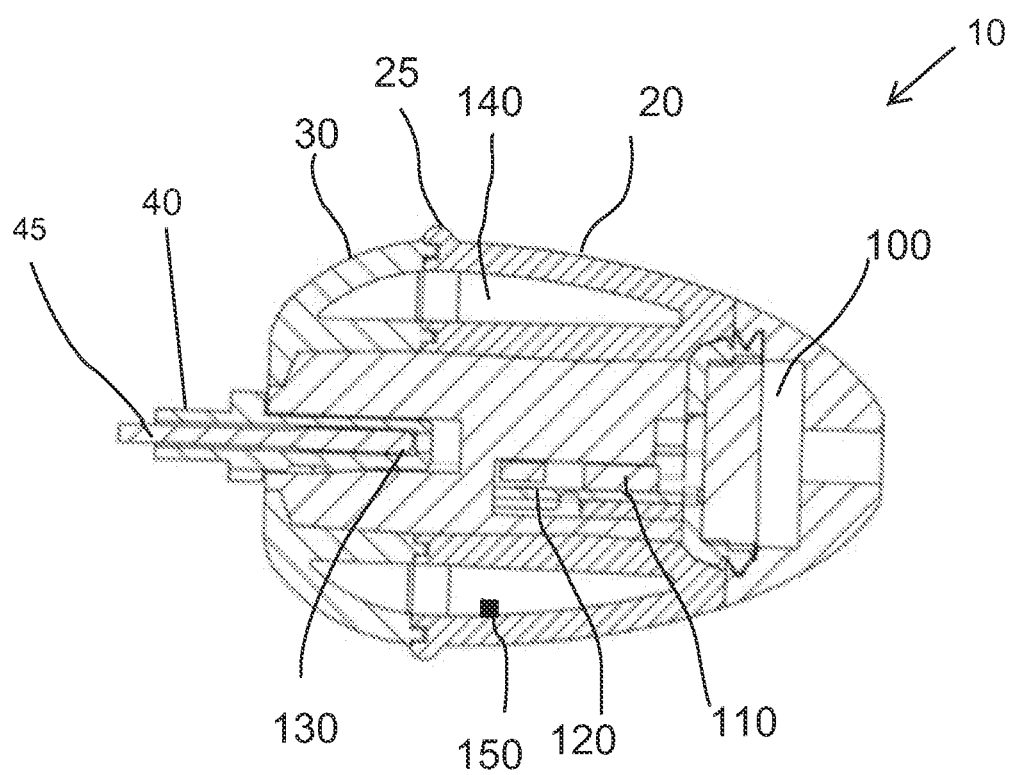
FIG. 2 is a cross-sectional view of the groundless user interface device of FIG. 1A along plane B-B.

FIG. 2 shows a cross section along plane B-B illustrated in FIG. 1A. As described herein, the groundless user interface device 10 can have three sections, the first section 20, the second section 30, and the third section 40. In some embodiments, features that enhance the grip may be provided on the external surface of the user interface device 10. FIG. 2 shows a lip 25. The user may use this lip 25 to grip the user interface device 10. Features such as the lip 25 may be used provide to position or orientation information to the user.

In the configuration illustrated in FIG. 2, a wire 45 extends from the third section 40. The wire 45 can couple to a magnetic position sensor 130. The magnetic position sensor 130 can be similar to magnetic position sensors known in the art. The magnetic position sensor 130 can determine the position of the groundless user interface device 10. The magnetic position sensor 130 can transmit the positional data to a control system, as described herein. As noted herein, other types of sensors including but not limited to wireless sensors may be used. Another set of sensors may be coupled to a sensor and electronics base 120. The sensor and electronics base 120 can optionally house one or more sensors. The sensor and electronics base 120 serves as a base for one or more sensors. The sensor and electronics base 120 holds one or more sensors in a fixed position relative to each other. In some embodiments, the sensor and electronics base 120 is disposed within the body of the groundless user interface device 10. The sensor and electronics base 120 can be disposed in the first section 20, the second section 30, and/or the third section 40. In some embodiments, one or more sensors can optionally be disposed outside of the body of the groundless user interface device 10. Sensors that may be coupled to the sensor and electronics base 120 include but are not limited to gyroscopes and accelerometers. Gyroscopes and accelerometers are able to measure the rotation and orientation (e.g., angular orientation) of the user interface device 10. The sensor and electronics base 120 can include at least one gyroscope. The sensor and electronics base 120 can include at least one accelerometer. The sensor and electronics base 120 can include at least one magnetometer. The sensor and electronics base 120 can include at least one 6 DOF (degree-of-freedom) sensor. The sensor and electronics base 120 can include at least one inertial measurement unit (IMU).

Any sensor known in the art can couple to the sensor and electronics base 120. The groundless user interface device 10 can include one or more sensors. The one or more sensors can determine the position and/or orientation of the groundless user interface device 10. The one or more sensors can detect motion of the groundless user interface device 10. The one or more sensors can determine if the user is holding the groundless user interface device 10 (e.g., by measuring impedance of a surface of the groundless user interface device 10, as described herein). The one or more sensors can determine if the user is applying pressure to the groundless user interface device 10 (e.g., by measuring pressure of a chamber of the groundless user interface device 10, as described herein).

In some embodiments, the groundless user interface device 10 includes a motor 100. Tactile feedback may be provided to the user by controlling the operation of the motor 100. For instance, the on-off times and speed of the motor 100 may provide information to the user. The motor 100 can optionally be a radial motor, as shown. Tactile feedback may also be provided by using rotating masses or vibrating motors instead of, or in addition to, the radial motor. The groundless user interface device 10 can include one or more mechanisms to provide tactile feedback. Tactile feedback can be provided by the motor 100. Tactile feedback can be provided by changing the pressure of a chamber, as described herein. Tactile feedback can be provided by vibration of the groundless user interface device 10. Other types of feedback are contemplated. The groundless user interface device 10 can produce sounds. For instance, the groundless user interface device 10 can produce a sound when the end effector is near a joint limit. The groundless user interface device 10 can emit light. For instance, the groundless user interface device 10 can emit light when in communication with a control system and/or the end effector.

In some embodiments, the motor 100 can convey a force or a torque to the user. The motor 100 can convey a force to the user so that the user can reorient the central axis 15 of the groundless user interface device 10 with a longitudinal axis of the end effector controlled by the groundless user interface device 10. As the user moves the groundless user interface device 10, the central axis 15 can become misaligned with the longitudinal axis of the end effector. The motor 100 can be activated to rotate within the groundless user interface device 10. In some embodiments, the motor 100 controls a rotating mass. A torque, moment, or force can be produced by the motor 100. This tactile feedback can indicate that the user should reorient the groundless user interface device 10. This tactile feedback can also provide information of the direction in which the user should move the groundless user interface device 10 to reorient the groundless user interface device 10. The motor 100 can convey information to the user when the groundless user interface device 10 is misaligned or starting to become misaligned with the end effector.

The faster the motor 100 spins within the groundless user interface device 10, the bigger the gyroscopic effect. The motor would apply a torque to the fingers of the user in the direction toward aligning the central axis 15 of the groundless user interface device 10 with the longitudinal axis of the end effector. The motor 100 would counteract or partially counteract the movement of the user when the user is moving the groundless user interface device 10 in a way that misaligns the axes. The motor 100 would encourage the user not to move a direction that misaligns the axes of the groundless user interface device 10 and the end effector. In this way, the groundless user interface device 10 would be more resistant to any disturbing forces that misalign the central axis 15 with a longitudinal axis of the end effector. The motor 100 can convey other information by providing a force or torque to the user. In some embodiments, the motor 100 can convey a joint limit by applying a force or torque.

One function commonly provided by the user interface devices is the ability to grasp, hold, or pinch an object. The groundless user interface device 10 described in FIGS. 1 and 2 can advantageously provide the ability to grasp, hold or pinch in a unique way. Referring to FIG. 2, a chamber 140 is illustrated in cross-section. The chamber 140 may be prefilled with fluid at a certain pressure. In some embodiments, the fluid is air. The chamber 140 may also have a pressure sensor 150. The chamber 140 can be circumferential within the groundless user interface device 10. In other embodiments, chamber 140 can be disposed about a portion of the circumference (e.g., 45° of the circumference, 90° of the circumference, 135° of the circumference, 180° of the circumference, 225° of the circumference, 270° of the circumference, etc.).

With this configuration, a grasping or holding motion can be implemented. The user may apply external pressure anywhere along the external surface of the chamber 140. In some embodiments, the chamber 140 is contained within a portion of the first section 20. In some embodiments, the chamber 140 is spaced away from the second section 30 and/or the third section 40. In some embodiments, the chamber 140 is spaced away from a tapered end of the first section 20. The pressure sensor 150 may sense the pressure change from the user pushing on the chamber 140. The pressure sensor 150 may convey the pressure change to the control system of the hyperdexterous robotic system. Subsequently, a proportionate amount of grasping or pinching force may be applied by the end effector associated with the user interface device 10.

Figure 3:
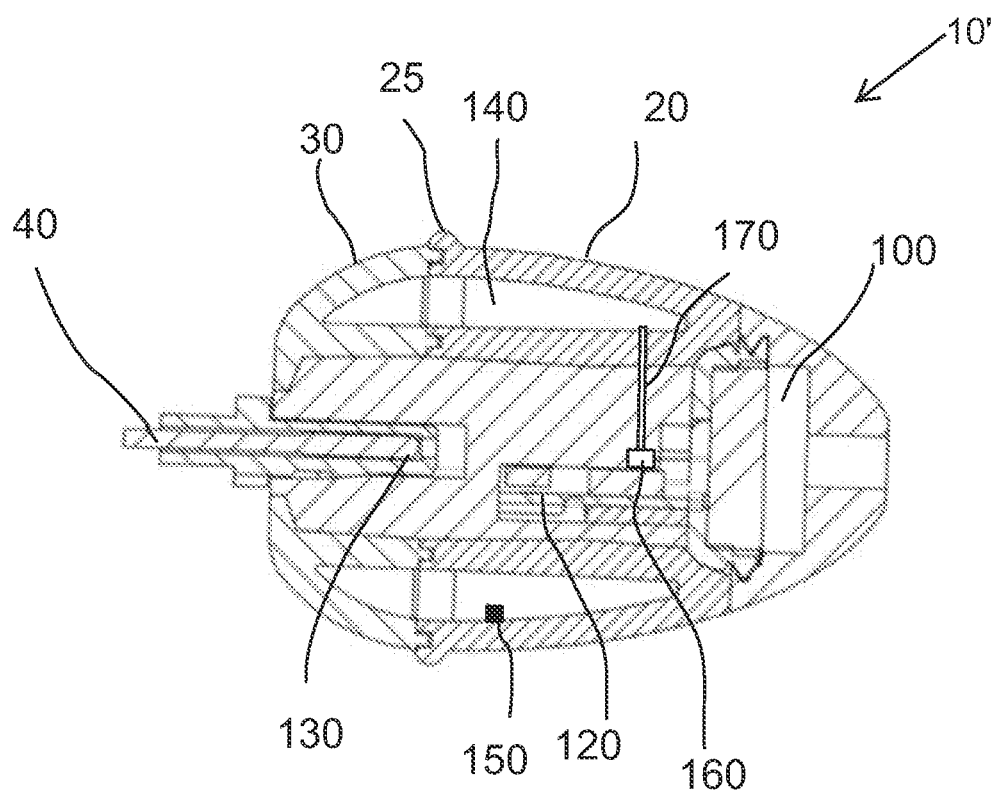
FIG. 3 is a cross-sectional view of an embodiment of a groundless user interface device.

In some embodiments, the chamber 140 may be used for providing tactile feedback. FIG. 3 shows user interface device 10'. The user interface device 10' can have some or all of the features described herein in relation to user interface device 10. The user interface device 10' can include a micro-pump 160. The micro-pump 160 can be coupled to the sensor and electronic base 120. The micro-pump 160 can be connected to the chamber 140 via a lumen as shown. The pressure within the chamber 140 may be controlled and modulated with the micro-pump 160. The micro-pump 160 can fill the chamber 140 with fluid to increase the pressure of the chamber 140. This can result in the user feeling the increase in pressure. The user interface device 10' can vent the chamber 140 to decrease the pressure of the chamber 140. In some embodiments, the micro-pump 160 can decrease the pressure. This can result in the user feeling the decrease in pressure.

In some methods of use, the end effector (not shown) is coupled to one or more force sensors. The force the end effector experiences may be translated to a proportionate pressure in the chamber 140. Thus if the end effector were to be in contact with a hard anatomical feature, the pressure within the chamber 140 can be increased. The operator may then find it harder to squeeze the user interface device 10'. Similarly, if the end effector was in contact with a soft anatomical feature, the pressure within the air chamber of the user interface device 10' may be decreased so that the operator finds it easy to squeeze the user interface device 10'. Thus, in this way by modulating the pressure in the chamber 140, tactile feedback may be provided to the operator. Additionally, if the end effector were to be in contact with another end effector or portion of the hyperdexterous robotic system, the pressure within the chamber 140 can be increased as well.

In related concepts, the method of modulating the pressure may be used to convey other types of information than specified above. In some methods of use, during the course of manipulating the hyperdexterous robotic system, the operator may maneuver one or multiple joints of the system such that these joints are operating at or close to their limits of operation. The pressure within the chamber 140 may be controlled and modulated to indicate such limits of operation. For instance, the pressure within the chamber 140 of the user interface device 10' can be made to be vibratory. The vibration may alert the operator that the system configuration may not be optimal at that time. Thus it can be seen that the chamber 140 may be used for conveying various types of information to the user.

The user interface device 10, 10' may be made of inexpensive materials such as but not limited to soft rubber and plastic. The sensor and the electronics may also be inexpensive, thus making the entire user interface device 10, 10' inexpensive. Another advantage of using inexpensive materials for the user interface device 10, 10' is that the design may be scalable in size. Thus user interface device 10, 10' of differing sizes may be manufactured to accommodate the various hand sizes of users. In some embodiments, the user interface device 10, 10' may be a disposable component (e.g., for use in a single surgical operation). Before the surgery, the preparation and set up of the system may include the step of opening a package containing the sterile user interface device 10, 10'.

The method may include the step of ensuring that that the control system of the hyperdexterous robotic system recognizes and accepts commands from the user interface device 10, 10'. The method may include additional steps to couple the user interface device 10, 10' to the hyperdexterous robotic system. In the case of a wired groundless user interface device, there may be a step of connecting a wire. The wire may originate from the hyperdexterous robotic system and thereafter couple to the user interface device 10, 10'. In the case of a wireless groundless user interface device 10, 10', there may be a step similar to pairing of headphones to a smartphone. For instance, the hyperdexterous robotic system may need to recognize the user interface device 10, 10' as a controller. The user may be required to enter an input or otherwise link the user interface device 10, 10' with the hyperdexterous robotic system. Further, there may also be a calibration step where the user is required to do certain manipulations with the user interface device 10, 10' so that the hyperdexterous robotic system may interpret the commands appropriately.

FIGS. 1-3 describe user interface device 10, 10' that may be described as self-contained in that all the electronic and the sensors may be contained within the body of the user interface device 10, 10'. In some embodiments, the power source is also contained within the body of the user interface device 10, 10'. A number of electronic components such as but not limited to sensors (gyroscopes, accelerometers, etc.), motors, pumps, power source may be disposed within the body of the user interface device 10, 10'. This may make the user interface device 10, 10' heavy which may lead to a loss of dexterity.

Figure 4:
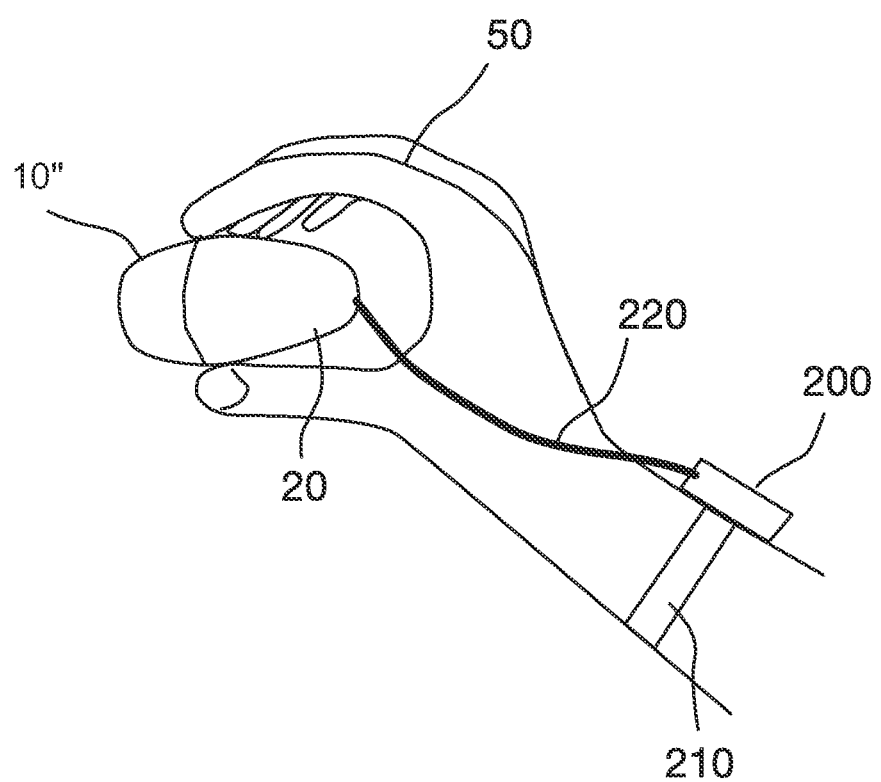
FIG. 4 schematically illustrates an embodiment of a groundless user interface device.

FIG. 4 shows an embodiment of the user interface device 10". The user interface device 10" can have some or all of the features described herein in relation to user interface device 10, 10'. The user interface device 10" advantageously redistributes the weight of the user interface device 10" so that dexterity may be maintained.

In FIG. 4, the operator is wearing a device 200 on his or her body. The device 200 may include an enclosure for various components of the user interface device 10". For instance, the device 200 may house various components including, but not limited to, a power source such as a battery pack, a processor, sensors and other electronics. The device 200 may also contain a micro-pump, similar to the micro-pump 160 shown in FIG. 3. The device 200 may be coupled to the user in a variety of ways. FIG. 4 shows a strap 210 coupling the device 200 to the body of the user. The device 200 may be coupled to the wrist of the user.

A cable 220 may extend between the device 200 and the first section 20 of the user interface device 10". The cable 220 may be composed of one or more wires (not shown). The wires may be used for carrying power to the user interface device 10". The wires may be used to transport signals or information between the user interface device 10" and the electronics or sensors within the device 200. The cable 220 may contain a flexible lumen for the passage of fluid (e.g., air) from the micro-pump. In this configuration, the user interface device 10" may be lightweight. The user interface device 10" can have the functionality as described herein in relation to user interface device 10, 10' due to the components that may be placed within the device 200.

In some embodiments, since the user interface device 10, 10', 10" discussed herein are not grounded as in a typical on-market system, they may be prone to accidental falls. This situation may arise when the operator mistakenly drops the user interface device 10, 10', 10". The user interface device 10, 10', 10" would be subject to rapid acceleration. Releasing the user interface device 10, 10', 10" may lead to injury to the patient if the end effector follows the user interface device 10, 10', 10" and rapidly accelerates.

To prevent injury to the patient, several techniques may be implemented. The acceleration of the user interface device 10, 10', 10" can be monitored (e.g., by one or more sensors, such as an accelerometer, in the UID 10, 10', 10"). As noted herein, the acceleration can indicate if the user has dropped the user interface device 10, 10', 10". In some techniques, if the acceleration is higher than a preset value, the control system of the hyperdexterous robotic system can prevent or limit movement of the end effector. In another technique, the impedance across the user interface device 10, 10', 10" may be monitored (e.g., by one or more sensors in the UID 10, 10', 10"). The impedance can be measured constantly or at regular intervals. The impedance can indicate if the user has contact with the user interface device 10, 10', 10". If the impedance crosses a threshold value indicating that the operator has lost contact with the user interface device 10, 10', 10", the hyperdexterous robotic system can prevent or limit movement of the end effector. For instance, if the impedance indicates that the user is not in contact with the user interface device, the hyperdexterous robotic system can limit any input of motion from the user interface device 10, 10', 10". These techniques may be used in combination so that multiple (e.g., redundant) techniques may prevent unwanted motion of the end effector due to motion of the user interface device 10, 10', 10".

Figure 5:
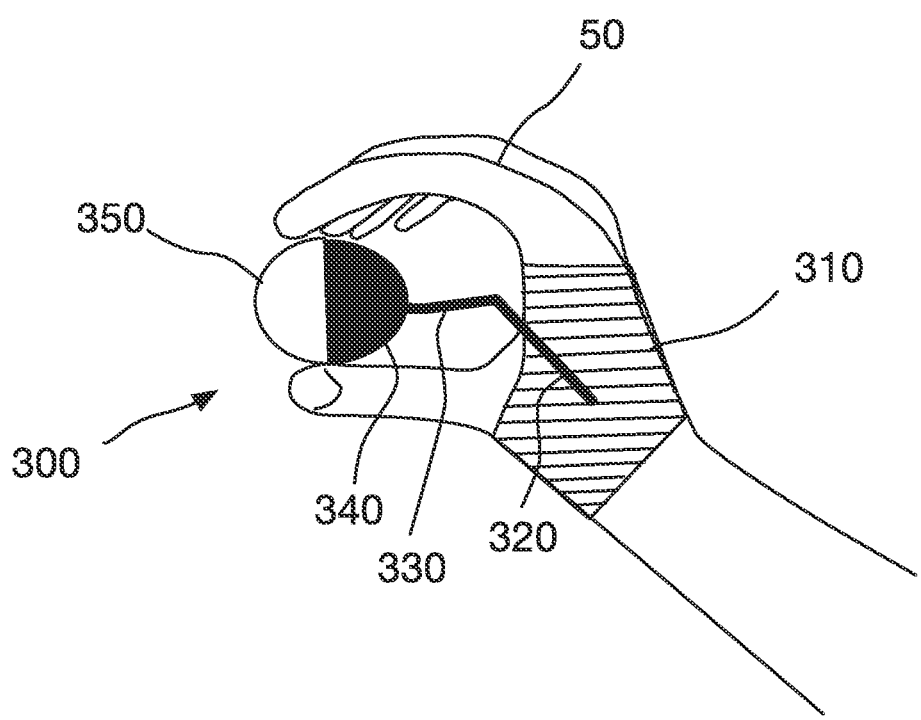
FIG. 5 schematically illustrates an embodiment of a body grounded user interface device.

FIG. 5 shows another embodiment of a user interface device 300. The user interface device 300 can have some or all of the features described herein in relation to user interface device 10, 10', 10". The user interface device 300 is not grounded to a platform or a console. Rather, the user interface device 300 is grounded to the body of the operator. The user interface device 300 is an embodiment of the body grounded user interface device describe herein. FIG. 5 illustrates how the user interface device 300 may be held advantageously by a human hand 50. In some embodiments, the hand of the operator provides the grounding. The user interface device 300 may include a grounding device 310. The grounding device 310 can be portable. The grounding device 310 may be coupled to or otherwise carried by the body of the operator. In some embodiments, the grounding device 310 is coupled to the hand of the operator. In some embodiments, the grounding device 310 is coupled to the palm of the operator. FIG. 5 shows the grounding device 310 may be wrapped around the palm. The grounding device 310 can be a strap. The grounding device 310 can be a partial glove. The grounding device 310 can be a jacket that surrounds a portion of the hand.

The grounding device 310 can be stiff or flexible. The grounding device 310 may be made of materials including, but not limited to, plastic. In some embodiments, the plastic may be custom molded to each operator's hand. One or more links may be coupled in a serial or parallel fashion to the grounding device 310. The parallel configuration is not shown in FIG. 5. In FIG. 5, a first link 320 is coupled to the grounding device 310. The first link 320 is coupled to a second link 330 in series. The links 320, 330 may be composed of lightweight but stiff rods. The links 320, 330 may be able to move relative to each other and/or relative to the grounding device 310. The links 320, 330 may be considered supporting structures that support the user interface device 300.

The second link 330 can be coupled to a section 340. The section 340 is shown in black in FIG. 5. The section 340 can have a hemispherical shape as shown. The section 340 may serve as a support for the user interface device 300. In some embodiments, the user interface device 300 may be in the shape of a ball. The section 340 may partially surround the user interface device 300. The user interface device 300 may be rotated freely within the section 340. In some embodiments, the section 340 includes an internal surface and the user interface device 300 is rotatable relative to the internal surface. With this configuration, the operator can roll the user interface device 300. The movement of links 320, 330 relative to each other may increase the degrees of freedom. More generally due to the ability of the links 320, 330 to also move relative to one another, the operator may be able to move the user interface device 300 in all six degrees of freedom. In addition, since the links 320, 330 may allow the operator to pull the user interface device 300 towards the palm, a seventh degree of freedom may also be available. This may be used for various purposes including but not limited to applying the grasping force to the end effector. The user interface device 300 may be a hollow and/or include one or more chambers as described herein. In some embodiments, the device 200 may include an enclosure for various components of the user interface device 300, as described herein. The device 200 may be coupled to the grounding device 310. The user interface device 300 may be lightweight. The user interface device 300 may be inexpensive as described herein. The user interface device 300 or parts of the user interface device 300 may be disposable. For example, user interface device 300 and the section 340 may be disposable. The grounding device 310 and/or the links 320, 330 may be reusable and/or not disposable. In some embodiments, convenient ways of coupling second link 330 and section 310 may be provided such as but not limited to magnetic coupling.

The configuration shown in FIG. 5 has many advantages. One advantage is that since it is a body grounded system, the chances of accidental fall of the user interface device 300 are minimized or eliminated. Another advantage is that the grounding device 310 may be used as a location to attach device 200 including components such as, but not limited to, electronics, sensors and a power source. Yet another advantage is that the grounding device 310 may be coupled with an optical tracking sensor as described in a companion disclosure International Application No. PCT/US2014/026115 filed Mar. 13, 2014, incorporated by reference. The optical tracking sensor can provide the position of the grounding device 310 and/or user interface device 300 relative to a reference point (not shown). The optical tracking sensor can be utilized to track the position of the grounding device 310 and/or user interface device 300. One skilled in the art may utilize others suitable sensors, mechanism or methods of tracking components of the user interface devices described herein.

Figure 6B:
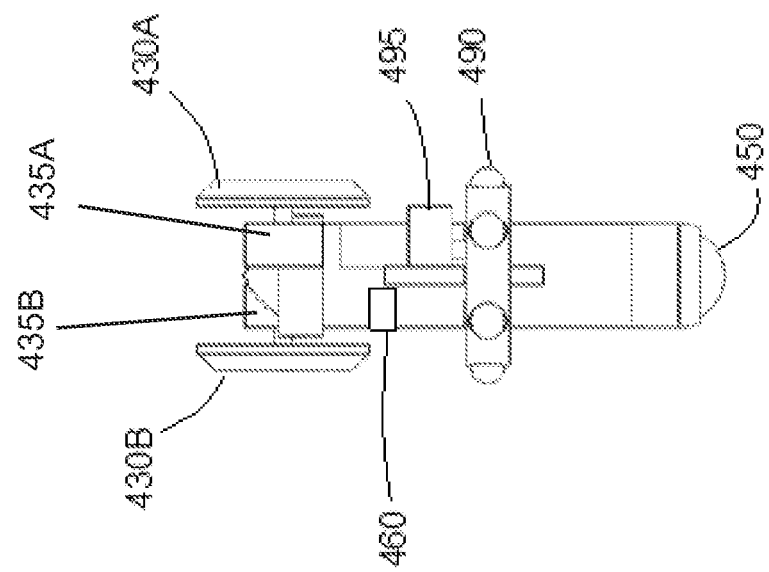
FIG. 6B schematically illustrates the chassis of FIG. 6A.
Figure 7:
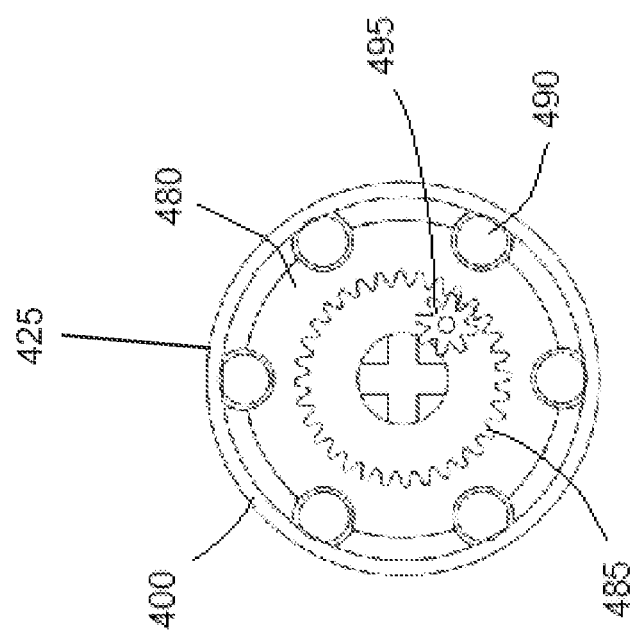
FIG. 7 is a cross-sectional view of a ring of the groundless user interface device of FIG. 6A.

FIGS. 6A, 6B, and 7 show another embodiment of the groundless user interface device. The groundless user interface device 400 includes a proximal end that can be held near the palm of the user's hand, similar to the device shown in FIG. 1B. The groundless user interface device 400 includes a distal end pointed away from the palm of the user. The central axis 475 of the user interface device 400 extends from the proximal end to the distal end. The central axis 475 can also be called an elongate axis or an axis of symmetry. The central axis 475 is along the length of the groundless user interface device 400. The groundless user interface device 400 has a transverse axis extending transverse (e.g., at 90 degrees) to the elongate axis 475. The transverse axis is along the width of the groundless user interface device 400. The groundless user interface device 400 has an elongate dimension along the elongate axis and a transverse dimension along the transverse axis. In some embodiments, the elongate dimension is greater than the transverse dimension. This creates an oblong shape of the groundless user interface device 400.

The groundless user interface device 400 includes a generally circular cross-section along the transverse axis creating a rounded exterior surface, as shown in FIG. 7. The exterior surface allows a user to rotate the groundless user interface device 400 with a hand of the user. The exterior surface allows the user to rotate the groundless user interface device 400 360 degrees. The user can turn the groundless user interface device 400 clockwise or counterclockwise.

The groundless user interface device 400 can attain a specific pitch, yaw and/or roll orientation in response to a parameter. In some embodiments, the parameter is the pitch, yaw and/or roll orientation of a robotic tool or end effector. In some embodiments, the parameter is the forces on the robotic end effector. In some embodiments, the parameter is a one or more system inputs. The system inputs can include whether the device is in drive mode or non-drive mode, as described herein. In the non-drive mode, the end effector is not responsive to commands from the user interface device as described herein.

The groundless user interface device 400 can include one or more actuators located inside the groundless user interface device 400. The actuators can be arranged so that they effect a motion of the external surface or a skin 425 of the groundless user interface device 400 relative to an internal chassis 440. The skin 425 is deformable, so that the motion of the chassis 440 within the skin 425 can change the shape of the skin 425. The ability to change the shape of the skin 425 permits the orientation of the groundless user interface device 400 to be controllable by software. The groundless user interface device 400 has a software-controllable orientation.

The one or more actuators located inside the groundless user interface device 400 can be arranged such that their coordinated movement causes a change in the overall shape of the groundless user interface device 400. The movement can be expansion or contraction. The movement can be any movement relative to the skin 425. The movements are a result of the software-controllable orientation of the groundless user interface device 400.

The groundless user interface device 400 can maintain alignment between the central axis 475 and the axis of an end-effector or tool of the robotic system. In some methods of operation, the orientation of the groundless user interface device 400 is actively modified to preserve the alignment of the groundless user interface device 400 and/or alignment of the central axis 475 with the end-effector that the user interface device 400 is associated with. The groundless user interface device 400 can include an external surface or skin 425. The groundless user interface device 400 can include a chassis 440. The chassis 440 can be disposed within the skin 425. The groundless user interface device 400 can have an ovoid shape, as shown in FIG. 6A. The groundless user interface device 400 can have a distinct longitudinal axis or central axis 475. The chassis 440 can move inside the skin 425. When the chassis 440 moves inside the skin 425, the user can perceive a change in the orientation of the central axis 475 of the groundless user interface device 400. In this way, the user can obtain information or feedback from the groundless user interface device 400.

Referring to FIG. 6A, the groundless user interface device 400 can have one or more wheels. In the illustrated embodiment, the groundless user interface device 400 has two wheels, 430A, 430B, but other configurations are contemplated (e.g., one wheel, two wheels, three wheels, four wheels, etc.). The groundless user interface device 400 can have one or more motors. In the illustrated embodiment, the groundless user interface device 400 has two motors 435A, 435B for driving the two wheels 430A, 430B. Other configurations are contemplated. The wheels 430A, 430B can optionally be coupled to one end of the chassis 440. The other end of the chassis 440 can optionally be coupled to a ball caster 450. Other devices or arrangement of devices that permit the chassis 440 to move are contemplated (e.g., rollers, wheels, casters, etc.). The groundless user interface device 400 is shown without the skin 425 in FIG. 6B. The configuration of wheels 430A, 430B and the caster 450 is one of many ways of implementing a two-degree-of-freedom system which is capable of being oriented inside an enclosed skin 425.

In some methods of use, the motors 435A, 435B are driven independently by control electronics. The groundless user interface device 400 can include one or more sensors such as but not limited to accelerometers, gyroscopes, pressure sensors. The control electronics and the sensors are shown as a single unit 460, but other configurations are contemplated. The groundless user interface device 400 can include a power source (not shown). The control electronics and the sensors can be disposed within the groundless user interface device 400, and in some embodiments, within or on the chassis 440. In some embodiments, the movement of the groundless user interface device 400 is controlled by the unit 460 within the groundless user interface device 400. The chassis 440 can be self-driven by the control electronics within the groundless user interface device 400. In some embodiments, the unit 460 receives control signals from an external control system. The control signals can operate the actuators to change the orientation of the central axis 475 or perform other movements as described herein. The chassis 440 can be driven by a system external to the groundless user interface device 400. The chassis 440 can be driven by control signals within or external to the groundless user interface device 400.

The chassis 440 can be moved within the skin 425. The two arrows 465 and 470 indicate that the chassis 440 can be tilted (arrow 465) or spun (arrow 470) about the central axis 475. The wheels 430A, 430B can allow the chassis 440 to be oriented in two degrees of freedom relative to the skin 425 of the groundless user interface device 400. As the chassis 440 moves within the skin 425, the central axis 475 can be tilted or rotated. During movement of the chassis 440, the skin 425 is stretched and deformed. The user can perceive that the orientation of the groundless user interface device 400 changes when the chassis 440 moves. In some methods of use, the user would perceive that the structure he or she is holding is pointing in a different direction.

The skin 425 of the groundless user interface device 400 can be deformable. The skin 425 can be made of flexible material. One example is ¹⁄₁₆" thick cast silicone rubber. The deformability allows the groundless user interface device 400 to assume any desired orientation. The deformability allows the central axis 475 to point in any direction. The deformability allows the groundless user interface device 400 to assume any pitch, yaw and/or roll of the central axis 475. The groundless user interface device 400 is ungrounded but capable of these functions.

In addition to the two degrees-of-freedom described above, the groundless user interface device 400 can optionally include another degree-of-freedom. The chassis 440 can be coupled to a ring 480. The groundless user interface device 400 can have one or more motors. In the illustrated embodiment, the groundless user interface device 400 has a motor 495 for rotating the ring 480. The ring 480 can rotate about chassis 440 which results in movement of the ring 480 inside the skin 425. The ring 480 can have an outer surface which contacts the inner surface of the skin 425. The outer surface of the ring 480 can have a lower coefficient of friction than the coefficient of friction of the wheels 430A, 430B. When the ring 480 is rotated, the chassis 440 will not rotate with respect to the skin 425, but instead the ring 480 will rotate with respect to the skin 425.

The ring 480 can have features 490 on the outer surface of the ring. The features can include ridges or detents. The features 490 may be felt by the user while the groundless user interface device 400 is being held. The features 490 may be rollers or balls to create a low coefficient of friction between the ring 480 and the skin 425. FIG. 7 shows a cross-section of the groundless user interface device 400 through the ring 480. The features 490 are shown as balls that contact the skin 425. The ring 480 can include an internal gear 480. The internal gear 485 can be driven by the ring motor 495. The features 490 can be rotationally asymmetric or rotationally symmetric. The additional degree of freedom can allow the groundless user interface device 400 to be positioned in any desired orientation. The additional degree of freedom can allow the groundless user interface device 400 to provide user feedback about position including roll position of the end effector. In some methods of use, the ring 480 may rotate inside the skin 425. The user can feel the position of the feature 490. The user can derive position information including roll information from the position of the feature 490. The groundless user interface device 400 can reflect or mimic the orientation of the end-effector to provide information or feedback to the user.

In an alternative embodiment, not shown, the skin 425 can be fixed to an internal structure with one or more actuators. The actuators can include an array of actuators in contact with the skin 425 of the groundless user interface device 400. The actuators can be solenoids, lead screws and motors, pressurized chambers, etc. The actuators can be small. The actuators can be controllably extended or retracted in response to the sensed orientation of the groundless user interface device 400. The sensed orientation can be provided by the sensors in the unit 460. The sensed orientation can be provided by the state of the system (e.g., drive mode, non-drive mode, etc.). The actuators can be extended and retracted in coordination to create an external skin 425 shape with the central axis 475. The actuators can be extended and retracted in coordination to create a shape, such as an ovoid shape. The actuators can be controlled to create the illusion that the orientation of the shape is fixed in space. The shape can appear fixed, despite the user rotating the groundless user interface device 400.

The groundless user interface device 400 can be controlled in many ways. As one example, the groundless user interface device 400 can operate in a drive mode. In the drive mode, the user is actively commanding the end effectors to perform some action. The groundless user interface device 400 can be moved by the user to move the end effector, as described herein with respect to other devices.

As one example, the groundless user interface device 400 can operate in a non-drive mode. In non-drive mode, the end-effector does not follow the orientation of the groundless user interface device 400 associated with the groundless user interface device 400. In non-drive mode, the end-effector is stationary. The end effector only moves while the groundless user interface device 400 is in drive mode. The chassis 440 can be driven in order to maintain alignment between groundless user interface device 400 and the end effector. In some methods of use, the chassis 440 can orient the central axis 475 in order to maintain alignment between groundless user interface device 400 and the end effector. When the groundless user interface device 400 is in non-drive mode, the user can reposition his or her hand to return to a more comfortable operating position and orientation. In the non-drive mode, the wheels 430A, 430B can be driven by the motors 435A, 435B such that the central axis 475 of the groundless user interface device 400 would maintain alignment (e.g. pitch and yaw) of the end effector. If the ring 480 were included, the wheels 430A, 430B can be driven by the motors such that the central axis 475 of the groundless user interface device 400 would maintain alignment (e.g. pitch, yaw, and roll) of the end effector. The user is free to move the groundless user interface device 400 in 3D space (e.g., x, y, z translation). As the user moves the groundless user interface device 400 in non-drive mode, the chassis 440 would move to orient the central axis 475. The effect is similar to a compass, as the central axis 475 would continue to align with the axis of the end effector. The central axis 475 or the axis of the ovoid body would remain pointing in the correct orientation to maintain alignment between the groundless user interface device 400 and the stationary end effector.

During drive mode, the groundless user interface device 400 can provide feedback regarding joint limits. The ability of the groundless user interface device 400 to reposition the central axis 475 in pitch, yaw, and roll can indicate the joint limit of the end effector. When the robotic tool is operating within the joint limits, the groundless user interface device 400 can be in drive mode. The motors in the groundless user interface device 400 are not active when the groundless user interface device 400 is operating within the joint limits. The six degree of freedom motions of the user would cause movement of the end-effector.

When one of the joint limits is reached, one or more motors of the groundless user interface device 400 would be actively driven. The chassis 440 of the groundless user interface device 400 would be driven in a direction that aligns the central axis 475 with the axis of the end-effector despite the user's attempts to further move the groundless user interface device 400. The groundless user interface device 400 can resist further movement in any of the roll, pitch or yaw directions.

For example, if the user attempts to roll the robotic tool past the joint limit, the motor controlling ring 480 on the chassis 440 may be activated. The motor may keep the ring 480 stationary in space with respect to the operator's frame of reference. The user would feel that the skin 425 of the groundless user interface device 400 was rotating around a stationary ring. This would provide feedback that the end-effector has reached a joint limit for rotation. The other motors 435A, 435B of the groundless user interface device 400 which control the wheels 430A, 430B can be driven when the end-effector encounters a joint limit in the pitch and yaw joints of the wrist of the robotic tool. As the user attempts to angle the end-effector past a joint limit, the chassis 440 would cease rotation in the direction the user desires. The motors controlling the chassis 440 would become active when the joint limit was reached. The chassis 440 can move such that the absolute orientation of the chassis 440 was constant, despite the changing orientation of the skin 425 held by the user. The absolute orientation of the chassis 440 can be given by the magnetic tracker, IMU, etc. This would provide feedback that the end-effector has reached a joint limit for pitch or yaw. In this mode of operation, the groundless user interface device 400 provides a direct haptic sense that the robot had reached a limit of travel in a particular angular direction.

Similar methods could be used to provide feedback to the user about force encountered by the end effector. For example, the jaw of the robotic tool may be used to palpate tissue by rotating the jaw until it presses on the tissue. Once the jaw encounters resistance, the groundless user interface device 400 may be driven in a way that communicates the force to the user. In some embodiments, the magnitude and/or orientation of the force are provided as feedback. The drive motors inside the groundless user interface device 400 may be pulsed to provide feedback. In some embodiments, the chassis 440 presses on a user's fingers and then retreats to the original orientation of the chassis 440. The motion of the chassis 440 can be in the direction of the force vector on the end effector. The motion of the chassis 440 can be in the frame of reference of the user. The motion of the force vector can be in the frame of reference of a robotic camera. The forward motion may be carried out in a shorter period of time, with higher acceleration, than the return of the chassis 440 to its original position. The user's fingers can be sensitive to the momentum of chassis 440 as the chassis 440 impact the skin 425, rather than the position or vibration of the chassis 440. In some methods of use, the groundless user interface device 400 increases the velocity of the chassis 440 in the direction of the applied force on the end effector and decreases the velocity when the chassis 440 returns to the actual position of the end effector. The groundless user interface device 400 may be able to communicate a force vector in a way that is easily interpreted by the user through the user's fingers. The magnitude and/or frequency of the pulsed motion may increase with increased force on the end effector.

In some embodiments, the user interface devices described herein can have a device for changing the shape of the body. The device can be a chassis 440 described herein. The device can be one or more actuators (e.g., one actuator, two actuators, three actuators, four actuators, a plurality of actuators, etc.). The one or more actuators can change the shape of the body of the user interface device. In some embodiments, the device can be one or more pressure chambers. The pressure chambers can be selectively filled with a fluid to change the shape of the user interface device. The volume of the pressure chambers can be increased or decreased based upon fluid entering the one or more chambers. In some embodiments, the shape change includes reorienting an axis of the body of the user interface device. In some embodiments, the shape change includes aligning the central axis of the user interface device with an axis of an end effector controlled by the user interface device.

The user interface devices described herein can control the motion of an end effector. The user interface devices described herein can be mapped to any section of the hyperdexterous surgical system. The user interface devices described herein can control different sections of the robotic arm or robotic tools. As one example, the user interface device can be used to reposition a handle midway along the robotic arm. The user interface devices described herein can have different modes of operation to control various components of the hyperdexterous surgical system. The user interface devices described herein may be mapped to virtual simulated tool motion. The user interface device can control a virtual end effector or any other virtual component of the hyperdexterous surgical systems. The user interface devices described herein can be mapped to a non-robotic object. Examples of non-robotic objects include an organ or other body structure. The surgeon may map the user interface device to the non-robotic object to receive haptic feedback about the non-robotic object.

The user interface devices describe herein may have non-surgical uses. The user interface device can be used for interacting with 3D virtual worlds. The user interface device can be mapped to any object within these worlds. The user interface device can provide the user with haptic feedback about the object that the user is virtually touching. The user interface devices can be used for a Computer Aided Drafting (CAD) program input. The user interface device can provide a virtual stylus or mapped to another tool. The ability of the user interface device to change shape, as described herein, may provide additional functionality for the user interface device in non-surgical uses. The changing of the shape may provide feedback related to the non-surgical use. The changing shape may provide feedback about objects encountered in the virtual world. The changing shape may provide feedback on the success or failure of a task. The changing shape may provide a sense of orientation or position within a virtual world. Other modes of feedback such as lights and sounds may also provide feedback to the user.

The method of using the groundless user interface device 400 can include controlling actuators within the groundless user interface device 400. The actuators can be motors that control one or more moveable features. The actuators can be used to orient a central axis of the groundless user interface device 400. The orientation of the central axis 475 can correspond with the orientation of the central axis of the end-effector. The orientation of the central axis 475 of the groundless user interface device 400 can be in the frame of reference of the user. The orientation of the axis of the end-effector can be in the frame of reference of a camera feed.

The method of using the groundless user interface device 400 can include providing feedback to the user. The orientation of the central axis 475 can provide information of the joint limits of the end-effector. The groundless user interface device 400 can provide feedback on the forces that the end effector encounters.

In some embodiment, the system may utilize optical sensors. The optical sensors can be used to sense proximity of objects, much like a proximity sensor, described below. In some embodiments, the optical sensor can track the user interface device. Other uses for optical sensors are contemplated. For instance, in some embodiments, the optical sensor can be located on user interface device 300. The hand of the user may obstruct the optical sensor mounted on the user interface device 300. The section 340 may partially surround the user interface device 300. The section 340 may obstruct the optical sensor mounted on the user interface device 300. In some embodiments, an optical sensor can be mounted to another portion of the body. The optical sensor can be mounted to the hand of the user. In some embodiments, the optical sensor can be mounted to the grounding device 310. The position of the grounding device 310 can serve as a proxy for the position of the user interface device 300. The grounding device may have fewer obstructions. The movement (e.g., translation, rotation) of the grounding device 310 can serve as a proxy for movement of the user interface device 300. In some embodiments, the optical sensor can be mounted to the links 320, 330.

As described earlier, the user interface devices 10, 10', 10", 300 have multiple sensors including but not limited to proximity sensors and a sensor array. The sensor array is a plurality of sensors. The sensor array can have the same or different types of sensors. Redundancy can be achieved by either duplication of the same sensor or different sensors. The same type of sensor measures the same parameter and achieves redundancy. Redundancy can also be achieved by using different types of sensors with different parameters are measured. After the measurements are taken, analysis can allow derived parameters to be checked.

A proximity sensor is a sensor that senses objects that are close but not necessarily touching the sensor. In some embodiments, the proximity sensors are optical sensors. The proximity sensors do not need to be optical, and other types of sensors are contemplated. Proximity sensors are commercially available. Proximity sensors are capacitive in nature. Proximity sensors provide the ability to sense if an object is near the user interface devices 10, 10', 10", 300. This may be advantageous in many situations. In some embodiments, the proximity sensors may sense the presence of fingers that hold the user interface devices 10, 10', 10", 300. If no objects (such as fingers) are sensed, the control system may command the hyperdexterous robotic system to enter a safe state. In the safe state, the hyperdexterous robotic system can limit any input of motion from the user interface device 10, 10', 10", 300. For instance, the end effectors can be held stationary in a position rather than follow the motion of the user interface device 10, 10', 10", 300. This can prevent harm to the patient from inadvertent movement of the end effectors (e.g., if the user inadvertently drops the user interface device 10, 10', 10", 200). In some embodiments, the proximity sensors may sense how the user interface device 10, 10', 10", 300 is being held. For instance, the proximity sensors may sense what gestures are being performed by the user. The gestures then may be mapped into system commands for the control system. For example, a gesture such as squeezing the user interface device 10, 10', 10", 300 may be used to zoom the camera in.

The multiple sensors of the user interface device 10, 10', 10", 300 can be used to provide redundant readings. In some embodiments, the redundancy may ensure safety operation of the hyperdexterous robotic system. For instance, the use of the proximity sensor and the impedance sensor may provide redundancy for detecting whether a user is holding the device.

The multiple sensors of the user interface device 10, 10', 10", 300 can be used to provide redundancy of function. In some embodiments, the sensors associated with the user interface device 10, 10', 10", 300 are different types. The user interface device 10, 10', 10", 300 can utilize the concept of split redundancy. As an example, a 6 DOF sensor can be disposed inside the user interface device 10, 10', 10", 300. The user interface device 10, 10', 10", 300 can also include an inertial measurement unit (IMU) that measures orientation and an optical tracker that measures translation. In some embodiments, one or more of the sensors can be disposed outside of the body of the user interface device 10, 10', 10", 300. For instance, the optical tracker can be coupled to grounding device 310.

The failure of the 6 DOF sensor may lead to undesired behavior of the end effector. To provide redundancy of function, another 6DOF sensor may be placed inside the user interface device 10, 10', 10". 300. However, the inertial measurement unit and the optical tracker, can provide the same function as the failed 6 DOF sensor. Each of the inertial measurement unit and the optical tracker can provide split redundancy. Together the inertial measurement unit and the optical tracker may provide the complete redundant functionality as the failed 6 DOF sensor. The inertial measurement unit and the optical tracker function as if a second 6DOF sensor were present. The inertial measurement unit may provide redundancy for the orientation readings of the 6 DOF sensor. The optical tracker may provide redundancy for the translatory component of the 6 DOF sensor. In some embodiments, a sensor can provide a redundant reading for the reading of another sensor. In some embodiments, a sensor can provide a redundant reading for part of the reading of another sensor. In some embodiments, each sensor can provide a redundant reading for the reading of another sensor. In some embodiments, each sensor can provide a redundant reading for part of the reading of another sensor. In some embodiments, a second sensor of the same type of sensor need not be included for redundancy.

Each sensor has different pitfalls. For instance, accelerometers may experience drift. The line of sight of the optical sensor may be obstructed. In some embodiments, the user interface device 10, 10', 10", 300 advantageously mitigates pitfalls by combining one or more different types of sensors. In some embodiments, the control system takes into account the geometry of the human hand. The control system can make assumptions based on the movement or position of the user interface device 10, 10', 10", 300 in relation to the hand.

Additional features of the system are described in U.S. Provisional No. 62/120,128, filed Feb. 24, 2015, and International Application No. PCT/US2015/042991 filed Jul. 30, 2015, each of which is hereby incorporated by reference herein in its entirety, which should be considered a part of this specification. These applications describe methods to decouple the coupled motions of the operator's hands. In some embodiments, the decoupling may be achieved by the use of additional tracking devices. For example, FIG. 8 illustrates a hyperdexterous surgical system having multiple sensors to decouple the coupled motion of the hands of the operator, in accordance with some embodiments.

Figure 8:
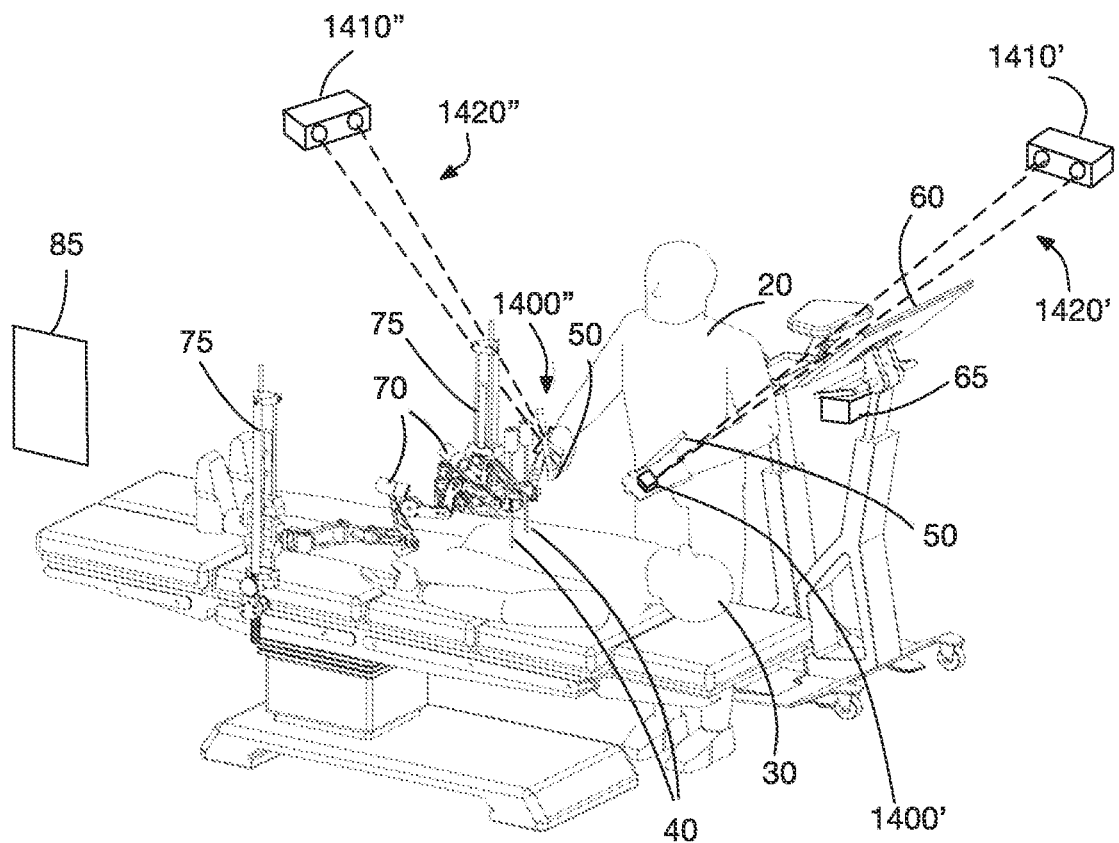
FIG. 8 illustrates a hyperdexterous surgical system having multiple sensors to decouple the coupled motion of the hands of the operator, in accordance with some embodiments.

As illustrated in FIG. 8, the operator 20 is seen operating the system with user interface device 50. The user interface device 50 can be groundless. The user interface device 50 can have any of the features of the user interface devices described herein, such as user interface device 10, 10', 10", 300, 400. The operator can also be seen coupled to devices 1400' and 1400". In some embodiments, these devices are situated on the back of the palms of the operator. In other embodiments, these devices may be situated at some other location along the operator's arm. In some embodiments, devices 1400' and 1400" may comprise one or more sensors (for example, sensors for magnetic tracking, sensors for inertial sensing, and/or the like). In other embodiments, such as those that use optical tracking, devices 1400' and 1400" may not contain any sensors, and may instead comprise one or more lights and/or reflective surfaces. The devices 1400' and 1400" can have any of the features of the devices described herein, including device 200 and grounding device 300.

Also seen in the FIG. 8 are two cameras 1410' and 1410". In some embodiments, camera 1410' is seen to have a direct line of sight to device 1400' and camera 1410" is seen to have a direct line of sight to device 1400". Devices 1400' and 1400" may have reflective surfaces, lights, pins or balls which along with the cameras 1400' and 1410" form the optical tracking system. Thus camera 1410' and device 1400' may track the position of the left hand of the operator 20 whereas camera 1410" and device 1400" may track the position of the right hand of the operator. Although devices 1400' and 1400" are illustrated at the back of the operator's hand, other locations may be chosen (for example, on user interface device 50, or on other locations of the operator's body). In some embodiments, the locations of devices 1400' and 1400" and cameras 1410' and 1410" may be reversed (for example, the cameras are located on the back of the operator's hand, while the devices are mounted with direct line of sight to the cameras). In some embodiments, other types of sensors may be utilized, such as magnetic tracking systems or visual tracking systems which are configured to recognize the shape of the operator's hand rather than a particular device or instrument affixed to the hand or body of the operator. Additionally, inertial sensing may be used (such as accelerometers), which would not require the presence of external tracking devices such as 1410' and 1410".

With this embodiment, the coupled translatory motion that the user interface device 50 may be subject to when the operator rolls the user interface device 50 with his or her fingers, may be decoupled and reduced or eliminated when the motion of the user interface device 50 is applied to the motion of the end-effectors. To explain this further, if the operator rolls the user interface device 50 (in some embodiments, it is immaterial if one or both hands are used) for example to apply a stitch to tissue, from the above discussion, it is expected that some translatory motion may couple into the user interface device 50. However using the supplemental tracking system described above or other tracking systems, the translatory motion can be measured. Assuming that the tracking system measures the same translatory motion that the user interface device 50 experiences, then the coupled translatory motion can be removed or eliminated from the motion applied to the end-effectors. In mathematical terms, if the motion of any one of the user interface device 50 is depicted by $_{UID\ base}^{UID}T$, then if the user interface device 50 experiences a roll and a translatory motion, in some embodiments it may be written as:

$$_{UIDbase}^{UID}T = \begin{bmatrix} _{UID\,Base}^{UID}R & _{UID\,Base}^{UID}P \\ 0 & 1 \end{bmatrix} \qquad \text{Eqn. 1}$$

The devices 1400' and 1400" may not experience any rolling motion when the user interface device 50 is subject to rolling motion by the operator using his or her fingers although it may experience the same translatory motion. It may also experience a motion which is mathematically related to the translatory motion of the user interface device 50 by a function determined by the kinematics of the human hand. Thus, assuming that the translatory motion of the user interface device 50 is the same as the translatory motion of the sensors on the back of the palm, the following equation may be written as:

$$_{UID\ base}^{UID}P = _{sensor\_base}^{back\_sensor}P \qquad \text{Eqn. 2}$$

where $_{UID\ Base}^{UID}P$ denotes the translatory motion of the user interface device 50 and $_{sensor\_base}^{back\_sensor}P$ denotes the translatory motion of the sensors 1400' or 1400". Now, the final applied motion of the robotic tool may be written as some general function φ of the two parameters: the motion of the user interface device 50 (which has coupled motion) and the motion of the sensors 1400' and 1400" in the back of the palm. Thus, $$_{Arm\ base}^{Grasper}M_{Final} = \varphi(_{UID\ Base}^{UID}T, _{UIDBase}^{UID}P) \qquad \text{Eqn. 3}$$

As specified in Eqn. 2, the translatory motion of the user interface device 50 is the same as the translatory motion of the device on the back of the palm. While calculating the final output in Eqn. 3, this component can be eliminated. Thus having an independent device that experiences only the translatory motion, allows decoupling of this motion from the user interface device motion.

In some embodiments, while two cameras 1410' and 1410" are illustrated in FIG. 8, only one camera may be needed. Other embodiments may include using sensors that are not optical in nature. Thus sensors 1400' and 1400" may be of various types including but not limited to electromagnetic sensors. In addition, while the illustration of the user interface device 50 in the figure looks like a long tubular structure, it is understood that in other embodiments, other shapes are possible.

It can be thus seen that with the above concepts, a method for orientation may be provided. In addition, a method to map the operator's natural motions to specific motions of the robotic tool is provided. Embodiments of these methods may advantageously improve the ease of use of system.

The method of use can include one or more of the following steps. The user may unwrap the user interface device from sterile packaging. The user may insert a wire into the user interface device. The user may insert a wire into a control system of a hyperdexterous robotic system. The user may connect a wire between the user interface device and the hyperdexterous robotic system. The user may wirelessly connect the user interface device and a control system of a hyperdexterous robotic system. The user may calibrate the user interface device with an end effector. The user may practice moving the end effector outside the body of the patient. The user may grasp the user interface device. The user interface device may measure the impedance on the surface of the user interface device when the user is contacting the user interface device. The user may move the user interface device from one location to another location. The motion of the user interface device from one location to another location may move an end effector from one location to another location. The movement may be the same distance or a proportionate distance. The user may move the user interface device about the central axis of the user interface device. The motion of the user interface device may move an end effector about the longitudinal axis of the end effector. The movement may be the same degree of rotation about the longitudinal axis or a proportionate degree. The user may apply a force to the user interface device. The application of force may cause the end effector to apply a force. The force may be a grasping force. The application of force may be the same amount of force or a proportionate amount of force. The user interface device may measure force with a pressure sensor.

The user interface device may provide feedback to the user. The user interface device may increase the pressure of a chamber of the user interface device. The user interface device may decrease the pressure of a chamber of the user interface device. The user interface device may increase the pressure when the end effector contacts hard materials such as bone or components of the hyperdexterous robotic system. The user interface device may decrease the pressure when the end effector contacts soft materials such as tissue. The user interface device may produce sounds. The user interface device may produce a warning sound when the end effector reaches a movement limit. The user interface device may produce a warning sound when the end effector is colliding or has the potential to collide with another object. The user interface device may produce a warning sound when the user interface device is moving too fast. The user interface may emit light. The user interface device may emit light when in communication with the end effector. The user interface device may emit light as a warning.

The user may couple a device to a portion of the body. The device may house various components of the user interface device. The device may reduce the weight of the user interface device. The user may couple the device to his or her wrist. The user may couple the device to his or her body with a strap.

The user may couple the user interface device with a portion of the body of the user. The user may rotate the user interface device within a section of an assembly. The user may couple the section to one or more links. The one or more links may have relative motion there between. The user may couple the one or more links to a grounding device. The user may couple the grounding device with a portion of the body of the user. The grounding device may be wrapped around the palm of the user. The grounding device may be a strap. The user interface device may have at least three degrees of freedom. The user interface device may have at least four degrees of freedom. The user interface device may have at least five degrees of freedom. The user interface device may have at least six degrees of freedom. The user interface device may have at least seven degrees of freedom. The user interface device may have as many degrees of freedom as the end effector under its control.

It may now be evident that the user interface devices described in this disclosure extend the utility of the hyperdexterous robotic system. The operator is not required to be stationary at one location. With the advanced user interface devices disclosed herein, the operator may assume the most optimal position in relation to the patient. Further, the operator can change his or her position during surgeon in relation to the patient. Many of the benefits of the hyperdexterous robotic system are enhanced due to these user interface devices such as the ability to perform manual and robotic surgery.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A groundless handheld portable user interface device, comprising:
    a body having an outer surface configured to be gripped by fingers of a user's hand and supported in free space solely by the user's hand to facilitate translocation and rotation of the body by the user's hand, wherein the body extends along a length defined by a longitudinal axis between a proximal end and a distal end, wherein the body extends along a width defined within a transverse plane that extends transverse to the longitudinal axis, the length being greater than the width of the body, wherein the outer surface includes a lip extending around the longitudinal axis along the transverse plane, and wherein the outer surface includes a first rotationally symmetric section proximal to the lip and the second rotationally symmetric section distal to the lip; and
    one or more sensors disposed within the body and configured to provide one or more of position information or orientation information of the body in free space to a control system of a surgical system;
    wherein the body is configured to receive control inputs from the user via one or more of translation of the body, rotation of the body, pressing of the outer surface with the user's fingers, or changing of the angular orientation of the longitudinal axis of the body, and wherein the user interface device is configured to provide an input to the control system to transform motion of the user interface device into motion of an end effector of a robotic arm of the surgical system.

2. The handheld portable user interface device of claim 1, wherein the body is configured to provide tactile feedback to the user via the outer surface of the body that is gripped by the fingers of the user's hand.

3. The handheld portable user interface device of claim 1, wherein the one or more sensors provides redundancy of function.

4. The handheld portable user interface device of claim 3, wherein the one or more sensors are of different types.

5. The handheld portable user interface device of claim 1, wherein the one or more sensors includes a proximity sensor.

6. The handheld portable user interface device of claim 1, wherein the outer surface is configured to be depressed by the user.

7. The handheld portable user interface device of claim 6, wherein the body comprises a chamber configured to be filled with a fluid, wherein depression of the outer surface by the user causes sensed pressure in the chamber to change, said change in sensed pressure communicated to the control system to convert the sensed pressure into a force applied by the end effector of the robotic arm controlled with the body.

8. The handheld portable user interface device of claim 7, wherein the body further comprises a pump configured to change the pressure of the chamber to provide tactile feedback to the user.

9. A groundless handheld user interface device, comprising:
 a body configured to be held in a user's hand and supported in free space solely by the user's hand, the body comprising an exterior surface configured to be gripped by fingers of the user's hand to facilitate translation and rotation of the body by the user's hand, wherein the exterior surface includes a lip extending around a longitudinal axis along a transverse plane, and wherein the exterior surface includes a first rotationally symmetric section proximal to the lip and a second rotationally symmetric section distal to the lip; and
 one or more sensors disposed within the body, the one or more sensors configured to provide one or more of position information or orientation information of the body in free space to a control system of a surgical system;
 wherein the body is configured to provide feedback to the user via the exterior surface of the body that is gripped by the user's fingers.

10. The handheld user interface device of claim 9, wherein the body is configured to receive control inputs from the user via one or more of translation of the body, rotation of the body, pressing of the exterior surface with the user's fingers, or changing of the angular orientation of the longitudinal axis of the body.

11. The handheld user interface device of claim 9, further comprising an internal chassis configured to move within the body to adjust an orientation of the longitudinal axis of the user interface device.

12. The handheld user interface device of claim 11, wherein the internal chassis moves relative to an outer skin of the body to attain a desired pitch and or yaw orientation of an axis of an end effector of the surgical system controlled by the handheld user interface device and communicates this to the user haptically.

13. The handheld user interface device of claim 11, wherein the internal chassis moves in one of the following ways selected from the group consisting of expansion, retraction, pulsing, and rotation.

14. The handheld user interface device of claim 11, wherein the internal chassis has one or more actuators that effect the motion of the internal chassis.

15. The handheld user interface device of claim 14, wherein the one or more actuators comprises a ring actuatable to attain a desired roll orientation of an axis of an end effector of the surgical system controlled by the handheld user interface device.

16. The handheld user interface device of claim 11, wherein the internal chassis adjusts pitch, yaw and/or roll orientation to maintain alignment of the longitudinal axis of the user interface device axis with an axis of an end effector of the surgical system controlled by the user interface device.

17. The handheld user interface device of claim 16, wherein the internal chassis adjusts pitch, yaw and/or roll orientation in response to forces on the end effector.

18. The handheld user interface device of claim 9, wherein the body comprises one or more actuators for changing of a shape of the body, or one or more pressure chambers for changing of the shape of the body.

19. The handheld portable user interface device of claim 1, wherein the outer surface of the body tapers radially inward from a circular cross-section at the lip to the proximal end.

20. The handheld portable user interface device of claim 1, wherein the proximal section is between the lip and the proximal end and has a proximal radius of curvature, and the distal section is between the lip and the distal end and has a distal radius of curvature different than the proximal radius of curvature.

21. The handheld user interface device of claim 9, wherein the proximal section has a proximal radius of curvature, and the distal section has a distal radius of curvature.

* * * * *